US010489717B2

(12) United States Patent
Mehta et al.

(10) Patent No.: US 10,489,717 B2
(45) Date of Patent: Nov. 26, 2019

(54) SYSTEM AND METHOD FOR PHARMACOVIGILANCE

(71) Applicant: Aetna Inc., Hartford, CT (US)

(72) Inventors: Rajesh Revachand Mehta, New York, NY (US); Henry George Wei, Larchmont, NY (US); Gregory Brian Steinberg, Dingmans Ferry, PA (US)

(73) Assignee: Aetna, Inc., Hartford, CT (US)

( * ) Notice: Subject to any disclaimer, the term of this patent is extended or adjusted under 35 U.S.C. 154(b) by 649 days.

(21) Appl. No.: 15/252,026

(22) Filed: Aug. 30, 2016

(65) Prior Publication Data

US 2017/0004275 A1 Jan. 5, 2017

Related U.S. Application Data

(63) Continuation-in-part of application No. 14/286,102, filed on May 23, 2014, now abandoned, which is a continuation of application No. 13/733,791, filed on Jan. 3, 2013, now Pat. No. 8,744,872.

(51) Int. Cl.
| G16H 50/30 | (2018.01) |
| G06N 7/00 | (2006.01) |
| G06F 19/00 | (2018.01) |

(52) U.S. Cl.
CPC ........... G06N 7/005 (2013.01); G06F 19/328 (2013.01)

(58) Field of Classification Search
CPC ......... G16H 10/60; G16H 50/70; G16H 50/30
See application file for complete search history.

(56) References Cited

U.S. PATENT DOCUMENTS

| 6,461,245 | B1 | 10/2002 | Morgan |
| D521,017 | S | 5/2006 | Jewitt et al. |
| D602,945 | S | 10/2009 | Watanabe et al. |
| D693,846 | S | 11/2013 | Daniel |
| D696,285 | S | 12/2013 | Hally |
| D728,611 | S | 5/2015 | Takano |
| D733,181 | S | 6/2015 | Manfredo et al. |
| D746,832 | S | 1/2016 | Pearcy et al. |
| 9,235,686 | B2 | 1/2016 | Jackson et al. |
| D760,248 | S | 6/2016 | Suarez |
| 9,413,807 | B1 | 8/2016 | Sherman et al. |
| D765,678 | S | 9/2016 | Goux |
| D769,899 | S | 10/2016 | Salazar Cardozo et al. |
| D769,918 | S | 10/2016 | Kim et al. |

(Continued)

OTHER PUBLICATIONS

"The Sentinel Initiative—National Strategy for Monitoring medical Product Safety"; May (2008) FDA.

*Primary Examiner* — John A Pauls
(74) *Attorney, Agent, or Firm* — Leydig, Voit & Mayer, Ltd.

(57) ABSTRACT

A method and system for analyzing a relationship between agents and clinical outcomes is disclosed. The method includes: receiving a selection of one or more agents; receiving a selection of one or more clinical outcomes; for each of the one or more agents, analyzing clinical data stored in a database to determine a number of occurrences of each of the one or more clinical outcomes when the agent is administered; for each of the one or more agents, calculating a risk score for each clinical outcome corresponding to the number of occurrences of the clinical outcome; and outputting the risk scores to a graphical display. The displayed information can also be scaled and filtered for ease of use. Also, the results may be stratified into sub-populations.

20 Claims, 16 Drawing Sheets

(56) References Cited

U.S. PATENT DOCUMENTS

| | | |
|---|---|---|
| D771,676 S | 11/2016 | Binder et al. |
| D772,245 S | 11/2016 | Mandawat et al. |
| D772,250 S | 11/2016 | Kohan et al. |
| D775,652 S | 1/2017 | Hoang et al. |
| D779,545 S | 2/2017 | Chen et al. |
| D781,303 S | 3/2017 | Lukanuski et al. |
| D786,900 S | 5/2017 | Parmar et al. |
| D788,126 S | 5/2017 | Evnin et al. |
| D789,952 S | 6/2017 | Maitlen et al. |
| D789,984 S | 6/2017 | Sun |
| D791,163 S | 7/2017 | Millares |
| D791,796 S | 7/2017 | Baudisch et al. |
| D792,904 S | 7/2017 | Nakaguchi et al. |
| D794,054 S | 8/2017 | Chaudhri |
| D795,891 S | 8/2017 | Kohan et al. |
| D799,500 S | 10/2017 | Selden et al. |
| D799,505 S | 10/2017 | Park et al. |
| D802,622 S | 11/2017 | Clymer et al. |
| D804,500 S | 12/2017 | Fischer et al. |
| 2003/0046110 A1 | 3/2003 | Gogolak |
| 2006/0206512 A1 | 9/2006 | Hanrahan et al. |
| 2007/0061611 A1 | 3/2007 | Mackinlay et al. |
| 2007/0250523 A1 | 10/2007 | Beers et al. |
| 2007/0294112 A1 | 12/2007 | Settimi |
| 2009/0319556 A1 | 12/2009 | Stolte et al. |
| 2009/0319891 A1 | 12/2009 | MacKinlay et al. |
| 2010/0223068 A1 | 9/2010 | Von Schweber et al. |
| 2011/0027291 A1 | 2/2011 | Schoeberl et al. |
| 2011/0302110 A1 | 12/2011 | Beers et al. |
| 2012/0084064 A1 | 4/2012 | Dzenis et al. |
| 2012/0179482 A1 | 7/2012 | Garms et al. |
| 2012/0271612 A1 | 10/2012 | Barsoum et al. |
| 2013/0016106 A1 | 1/2013 | Yip et al. |
| 2013/0054621 A1 | 2/2013 | Kretz et al. |
| 2013/0132444 A1 | 5/2013 | Chen et al. |
| 2014/0282147 A1 | 9/2014 | Kim et al. |
| 2014/0282163 A1 | 9/2014 | MacKinlay et al. |
| 2014/0282187 A1 | 9/2014 | Mackinlay et al. |
| 2015/0278213 A1 | 10/2015 | Anand et al. |
| 2015/0278214 A1 | 10/2015 | Anand et al. |
| 2015/0278371 A1 | 10/2015 | Anand et al. |
| 2016/0070430 A1 | 3/2016 | Kim et al. |
| 2016/0070451 A1 | 3/2016 | Kim et al. |
| 2016/0274750 A1 | 9/2016 | Stewart |
| 2016/0342292 A1 | 11/2016 | Stewart |
| 2016/0343154 A1 | 11/2016 | Stewart |
| 2017/0010776 A1 | 1/2017 | Stewart |
| 2017/0010785 A1 | 1/2017 | Stewart |
| 2017/0010786 A1 | 1/2017 | Stewart |
| 2017/0010792 A1 | 1/2017 | Stewart |

SYSTEM AND METHOD FOR PHARMACOVIGILANCE

CROSS-REFERENCE TO RELATED APPLICATIONS

This patent application is a continuation-in-part of U.S. patent application Ser. No. 14/286,102 filed on May 23, 2014, which is a continuation of U.S. patent application Ser. No. 13/733,791 filed on Jan. 3, 2013 (now issued as U.S. Pat. No. 8,744,872), both of which are hereby incorporated by reference in their entireties.

FIELD

This disclosure relates generally to the field of health care management and, more specifically, to a system and method for pharmacovigilance.

BACKGROUND

Pharmacovigilance is the science of collecting, monitoring, researching, assessing, and evaluating information from healthcare providers and patients on the adverse effects of medications with a view towards identifying hazards associated with the medications and preventing harm to patients.

A typical health care system includes a variety of participants, including doctors, hospitals, insurance carriers, and patients, among others. These participants frequently rely on each other for the information necessary to perform their respective roles because individual care is delivered and paid for in numerous locations by individuals and organizations that are typically unrelated. As a result, a plethora of health care information storage and retrieval systems are required to support the heavy flow of information between these participants related to patient care. Critical patient data is stored across many different locations using legacy mainframe and client-server systems that may be incompatible and/or may store information in non-standardized formats. To ensure proper patient diagnosis and treatment, health care providers often request patient information by phone or fax from hospitals, laboratories, or other providers. Therefore, disparate systems and information delivery procedures maintained by a number of independent health care system constituents lead to gaps in timely delivery of critical information and compromise the overall quality of clinical care. Since a typical health care practice is concentrated within a given specialty, an average patient may be using services of a number of different specialists, each potentially having only a partial view of the patient's medical status.

Moreover, pharmacovigilance is facing increased pressure from regulators and academics who are mining real-world databases for safety signals. Some factors affecting the pharmacovigilance landscape include: an increasing use of real-world data by regulators; heightened expectations of manufacturers from the FDA (Food and Drug Administration), public, and academics/investigators; externalization of safety data (e.g., EMR (electronic medical records); and emergence of pharmacovigilance as an applied science.

There are certain limitations to the way in which pharmacovigilance is currently being implemented. Firstly, pharmacovigilance, or drug surveillance, is typically done by "ad hoc" reporting, where a physician independently identifies patients that have a problem with a certain drug and report this singular instance to the FDA. The FDA then accumulates this information and communicates with pharmaceutical manufacturers. This process is inefficient and ineffective.

To overcome some of the drawbacks of the ad hoc approach, the FDA has implemented the "Sentinel" and "Mini Sentinel" initiatives. However, these initiatives look at retrospective and/or historical data to perform drug surveillance.

Accordingly, there remains a need in the art for a system and method for pharmacovigilance that overcomes the drawbacks and limitations of current approaches.

SUMMARY

Some embodiments provide systems, methods, and computer-readable storage media for displaying a graphical representation of relationships between a plurality of agents and a plurality of clinical outcomes. A method includes: receiving, by a processor included in a computing device, a selection of a plurality of agents; receiving, by the processor, a selection of a plurality of clinical outcomes; analyzing, by the processor, clinical data stored in a database to determine a number of occurrences for each clinical outcome when one or more agents are administered to a plurality of patients having a first clinical condition; calculating, by the processor, for each agent-clinical outcome pairing, a count for a number of patients having the first clinical condition, that were administered the agent of the agent-clinical outcome pairing, and had the clinical outcome of the agent-clinical outcome pairing; calculating, by the processor, for each agent-clinical outcome pairing, a relative risk score for patients having the first clinical condition, that were administered the agent of the agent-clinical outcome pairing, and had the clinical outcome of the agent-clinical outcome pairing; calculating, by the processor, for each agent-clinical outcome pairing, a statistical significance value for the relative risk score corresponding to the agent-clinical outcome pairing; and, displaying, in a graphical user interface on the display device, a two-dimensional grid in which one or more agents are displayed in a first axis and one or more clinical outcomes are displayed in a second axis, wherein a given agent-clinical outcome pairing is displayed in the graphical user interface if the count for the agent-clinical outcome pairing exceeds a first threshold, the relative risk score for the agent-clinical outcome pairing exceeds a second threshold, and the statistical significance value for the relative risk score for the agent-clinical outcome pairing exceeds a third threshold.

Some embodiments provide systems, methods, and computer-readable storage media for analyzing a relationship between an agent and a clinical outcome. A method includes: receiving, by a processor included in a computing device, a selection of a first agent; receiving, by the processor, a selection of a first clinical outcome; categorizing, by the processor and based on one or more stratification factors, a plurality of patients into a plurality of stratification categories, wherein each patient in the plurality of patients is associated with a first clinical condition and is administered the first agent; analyzing, by the processor, clinical data stored in a database to determine a number of occurrences of the first clinical outcome when the first agent is administered to the plurality of patients; calculating, by the processor, for the first agent and the first clinical outcome, a first set of risk scores, wherein a separate risk score corresponds to each of the plurality of stratification categories, and wherein calculating the risk score for a given stratification category includes measuring a statistical significance of a relationship between the first agent and the clinical outcome for the patients included in the given stratification category; displaying, in a graphical user interface on the display device, a two-dimensional grid in which the first clinical outcome is displayed in a first axis and the plurality of stratification categories are displayed in a second axis; and, displaying, in the graphical user interface, for each stratification category in which the first clinical outcome is observed, a graphical element corresponding to a relative risk score for the combination of first agent and the first clinical outcome for the stratification category.

DETAILED DESCRIPTION

Figure 1:
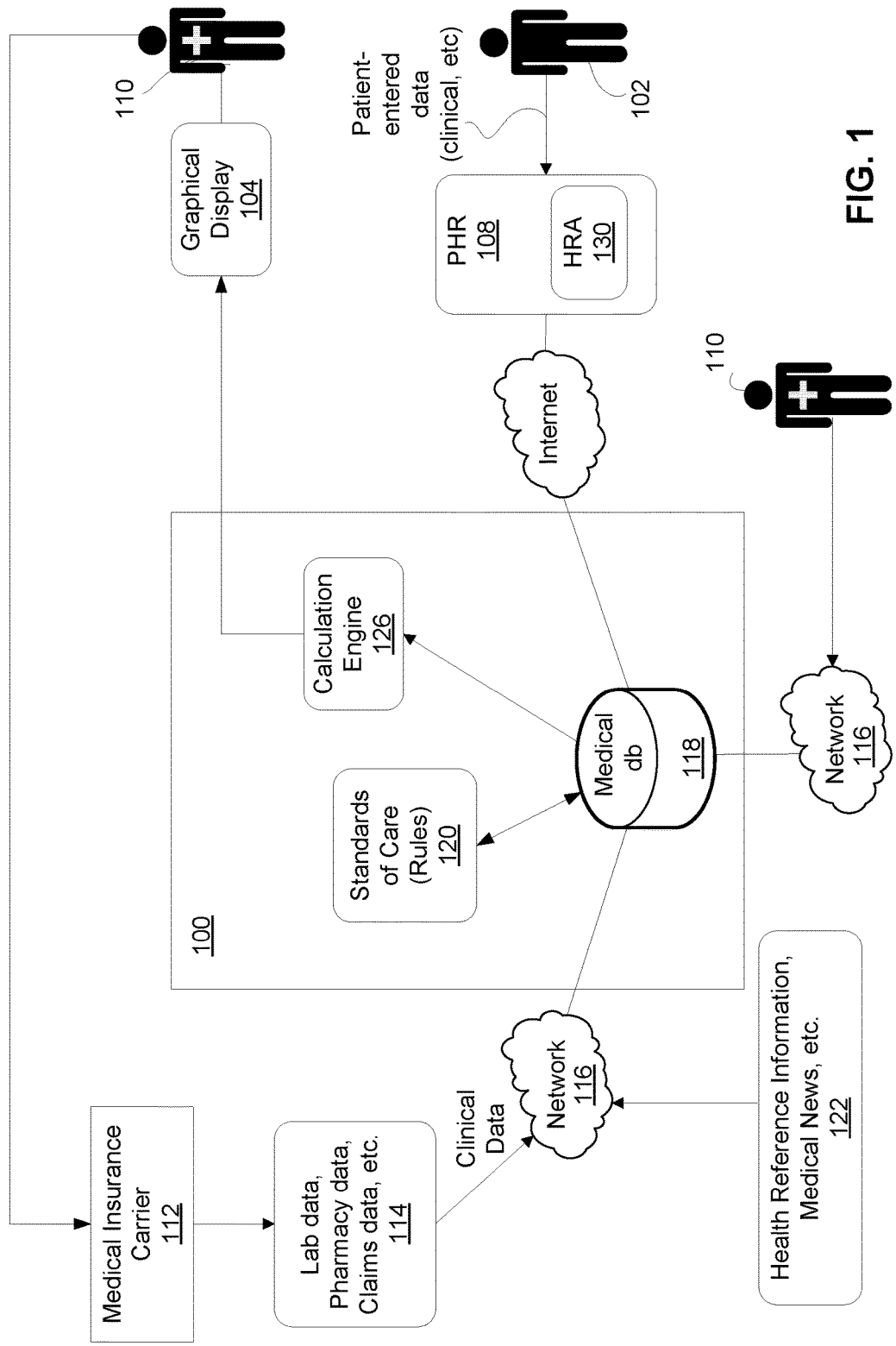
FIG. 1 is a schematic diagram illustrating an overview of a system for analyzing a relationship between one or more agents and one or more clinical outcomes, in accordance with an embodiment of the disclosure.

Embodiments of the disclosure provide a system and method for pharmacovigilance. According to some embodiments, health related clinical or other data is stored in one or more databases. The clinical data may include, for each patient, demographic data, diagnostic codes (e.g., ICD (International Statistical Classification of Diseases and Related Health Problems) 9 and/or ICD 10), procedure codes (e.g., CPT (Current Procedural Terminology) codes, HCPCS (The Healthcare Common Procedure Coding System) codes), medication and prescription data (e.g., NDC (National Drug Code) and GPI (Generic Product Identifier)), and lab data (e.g., LOINC (Logical Observation Identifiers Names and Codes), among others. Clinical data may also include data from electronic medical records (EMRs) and/or publicly available database (e.g., Medwatch). Other data may include medical cost data, including pharmaceutical costs, care and treatment costs, and the like. Other data may include genetic information data and/or data from patient devices, such as computers, smart phones, and wearable devices (e.g., fitness trackers, heart rate monitors, and the like. Further, other data may include data from consumer activity databases such as credit card transaction databases, online search activity databases and social media activity databases (e.g., Facebook, Twitter). Further still, other data which may be considered, in an adverse event surveillance embodiment of the present disclosure, includes demographic data, geographic data (e.g., zip code), employment data, and/or family relationship data.

A processor in a computer system is configured to receive a selection of one or more agents (e.g., drugs) and one or more clinical outcomes. Examples of clinical outcomes include, for example, adverse events, productivity of a workforce, violent crimes in a population, etc. The processor is configured to calculate a risk score for the one or more clinical outcomes in relation to the one or more agents. In one or more embodiments, the processor is configured to calculate a risk score for the one or more clinical outcomes based on a prioritized, weighted list of data sources (e.g., where clinical data is weighted relatively higher than consumer activity data). According to various embodiments, the risk score may be an absolute risk or a relative risk. In some embodiments, one or more of a Chi-squared statistical analysis and a P-value statistical analysis may also be performed to confirm or reject the observed calculations.

Accordingly, some embodiments provide a proactive, prospective, and ongoing approach to pharmacovigilance. The database from which the analysis is performed is continuously being updated with new clinical data. For example, medical claims data may be entered into the database within 48 hours of an insurance carrier receiving information about the treatment. In some embodiments, the database from which the analysis is performed is continuously (or substantially continuously) updated from claims databases of a plurality of healthcare organizations and/or insurance carriers.

Some embodiments disclosed herein provide a proactive and automated signal detection, surveillance, and reporting system with standardized reporting. Examples of reporting systems used with embodiments of the disclosure include providing reporting interfaces that report information to drug manufacturers, the FDA (Food and Drug Administration), to the public (e.g., label warning updates), to product liability insurers, and/or to individual patient patients (e.g., Patient A is on drug X, but the system detected that there are side effects when Drug X is taken with apples). In some embodiments, notices may be sent directly to registered patient devices (e.g., mobile devices, etc.). Advantageously, reporting on information may be helpful to drug manufacturers or health plan organizations for: performing second-level confirmatory analytics, in reapplying for additional off-label uses (e.g., different patient populations (e.g., by gender, ethnicity, age band, etc.), in exonerating a drug for broader use within the population (e.g., by narrowing the risk to particular genders, ethnicity, age bands, etc.), in applying for an unanticipated use (e.g., where an unanticipated benefit or harm has been identified), for re-pricing (e.g., reports can be used by health plans to inform negotiations for "value based" pricing of drugs; can inform drug manufacturers on higher value for drugs with new/expanded uses), for refining criteria for plan benefit eligibility, and for remarketing a drug, among other uses.

Some embodiments provide real-time monitoring due to rapid adjudication and incorporation of claims data into analytic database, and a signal validation system that can exonerate or stratify risk in near real-time and identify potential benefits, versus an industry average of six to nine months.

Turning to the figures, FIG. 1 is a schematic diagram illustrating an overview of a system for analyzing a relationship between one or more agents and one or more clinical outcomes, in accordance with an embodiment of the disclosure. A health care organization 100 collects and processes a wide spectrum of medical care information relating to a patient 102 in order to analyze the relationship between one or more agents and one or more clinical outcomes. A personal health record (PHR) 108 of a patient 102 may be configured to solicit the patient's input for entering additional pertinent medical information, tracking follow-up actions, and allowing the health care organization 100 to track the patient's medical history. For example, the patient 102 may enter data through a laptop or desktop computer, through the patient's mobile device, or via a biometric device worn by the patient 102 (e.g., a fitness tracker or smart watch).

When the patient 102 utilizes the services of one or more health care providers 110, a medical insurance carrier 112 collects the associated clinical data 114 in order to administer the health insurance coverage for the patient 102. Additionally, a health care provider 110, such as a physician or nurse, enters clinical data 114 into one or more health care provider applications pursuant to a patient-health care provider interaction during an office visit or a disease management interaction. Clinical data 114 originates from medical services claims, pharmacy data, as well as from lab results, and includes information associated with the patient-health care provider interaction, including information related to the patient's diagnosis and treatment, medical procedures, drug prescription information, in-patient information, and health care provider notes, among other things. The medical insurance carrier 112 and the health care provider 110, in turn, provide the clinical data 114 to the health care organization 100, via one or more networks 116, for storage in one or more medical databases 118. The medical databases 118 are administered by one or more server-based computers associated with the health care provider 100 and comprise one or more medical data files located on a computer-readable medium, such as a hard disk drive, a CD-ROM, a tape drive, or the like. The medical databases 118 may include a commercially available database software application capable of interfacing with other applications, running on the same or different server based computer, via a structured query language (SQL). In an embodiment, the network 116 is a dedicated medical records network. Alternatively, or in addition, the network 116 includes an Internet connection that comprises all or part of the network.

In some embodiments, an on-staff team of medical professionals within the health care organization 100 consults various sources of health reference information 122, including evidence-based preventive health data, to establish and continuously or periodically revise a set of clinical rules 120 that reflect best evidence-based medical standards of care for a plurality of conditions. The clinical rules 120 are stored in the medical database 118.

To supplement the clinical data 114 received from the insurance carrier 112, the PHR 108 allows patient entry of additional pertinent medical information that is likely to be within the realm of patient's knowledge. Examples of patient-entered data include additional clinical data, such as patient's family history, use of non-prescription drugs, known allergies, unreported and/or untreated conditions (e.g., chronic low back pain, migraines, etc.), as well as results of self-administered medical tests (e.g., periodic blood pressure and/or blood sugar readings). Preferably, the PHR 108 facilitates the patient's task of creating a complete health record by automatically populating the data fields corresponding to the information derived from the medical claims, pharmacy data and lab result-based clinical data 114. In one embodiment, patient-entered data also includes non-clinical data, such as upcoming doctor's appointments. In some embodiments, the PHR 108 gathers at least some of the patient-entered data via a health risk assessment tool (HRA) 130 that requests information regarding lifestyle, behaviors, family history, known chronic conditions (e.g., chronic back pain, migraines, etc.), and other medical data, to flag individuals at risk for one or more predetermined medical conditions (e.g., cancer, heart disease, diabetes, risk of stroke, etc.) pursuant to the processing by a calculation engine 126. Preferably, the HRA 130 presents the patient 102 with questions that are relevant to his or her medical history and currently presented conditions. The risk assessment logic branches dynamically to relevant and/or critical questions, thereby saving the patient time and providing targeted results. The data entered by the patient 102 into the HRA 130 also populates the corresponding data fields within other areas of PHR 108. The health care organization 100 aggregates the clinical data 114 and the patient-entered data, as well as the health reference and medical news information 122, into the medical database 118 for subsequent processing via the calculation engine 126.

The health care organization 100 includes a multi-dimensional analytical software application including a calculation engine 126 comprising computer-readable instructions executed by one or more processors for performing statistical analysis on the contents of the medical databases 118 in order to analyze a relationship between one or more agents and one or more clinical outcomes. The relationships identified by the calculation engine 126 can be presented in a graphical display 104, e.g., to the healthcare provider 110 and/or medical insurance carrier 112 and/or to the government (e.g., FDA) and/or to the patient 102.

After collecting the relevant data, the calculation engine 126 receives a selection of one or more agents. In one example implementation, the agents are prescription drugs. The calculation engine calculates a risk of occurrence of one or more clinical outcomes for each of the one or more agents. In some embodiments, the calculation engine 126 also receives a selection of an "indication" (e.g., a medical or clinical condition, disease, etc.) experienced by a portion of the population of patients. In one implementation, a drug may be exonerated from causing a clinical outcome for specific subgroups of a population (e.g., those that also have the "indication") or possibly overall (e.g., entire population). In some implementations, a drug may be exonerated when taken in combination with other criteria present; for example, when taken with other drugs, when taken with certain foods, or when exercise is detected, among others. In another example implementation, the calculation engine 126 may determine that certain adverse events occur mostly in off-label use. "Off-label" use refers to non-recommended uses of a drug, such as non-FDA approved uses. In another implementation, calculation engine 126 may determine how a drug's safety profile compares to other drugs within the same class of drugs. Other use cases are also within the scope of embodiments of the disclosure, as described in greater detail herein. In further embodiments, the calculation engine 126 may determine that a drug is "protective" relative to a certain clinical outcome for a certain subpopulation of patients, as described in greater detail herein.

For example, embodiments disclosed herein can provide "comparative effectiveness" information by directly comparing multiple pharmacologically similar agents against varied and multiple health outcomes of interest, allowing for inferences to be made about the comparative risks and benefits of these agents. In some embodiments, a comparison process may include the steps of identifying a subgroup based on age, gender, race, ethnicity, geography or other categories, and comparing the subgroup to other subgroup(s) based on the same categories to determine if a given agent or intervention is more or less effective (or harmful) as compared to another agent or intervention within a given subgroup. In another embodiment, a comparison process may be employed to simultaneously determine risks and benefits associated with a given agent in a given subgroup, and output a graphical summary which can be used to inform a risk/benefit determination by individual patients and/or healthcare providers.

While the entity relationships described above are representative, those skilled in the art will realize that alternate arrangements are possible. In one embodiment, for example, the health care organization 100 and the medical insurance carrier 112 is the same entity. Alternatively, the health care organization 100 is an independent service provider engaged in collecting, aggregating, and processing medical care data from a plurality of sources to provide a personal health record (PHR) service for one or more medical insurance carriers 112. In yet another embodiment, the health care organization 100 provides PHR services to one or more employers by collecting data from one or more medical insurance carriers 112. In one embodiment, an insurance carrier computer system executes the calculation engine 126. In yet another embodiment, a third party computer system receives medical care (and other) data from a plurality of sources, including multiple medical insurance carriers and health care organizations, and executes the calculation engine 126.

Figure 2:
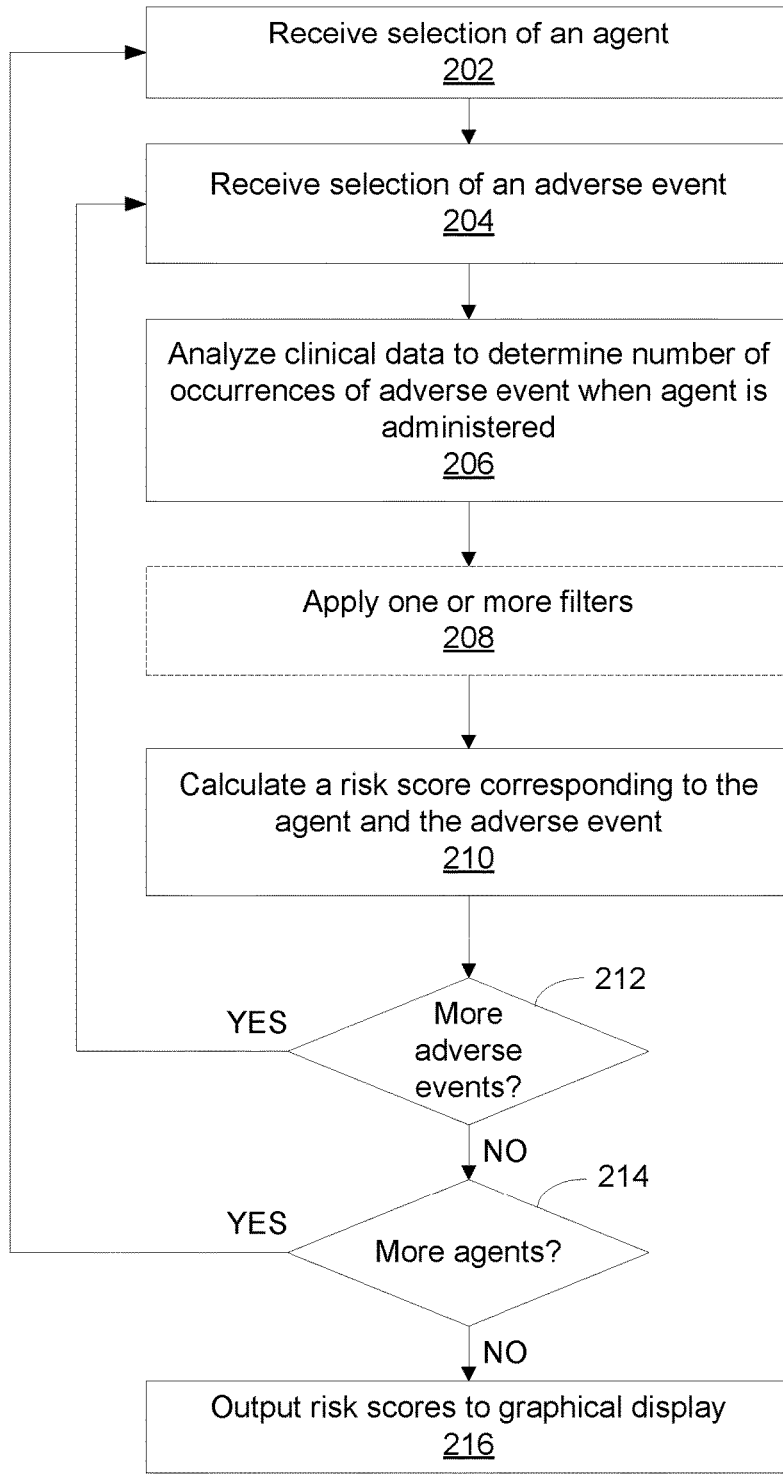
FIG. 2 is a flow diagram illustrating a method for analyzing a relationship between one or more agents and one or more clinical outcomes, in accordance with an embodiment of the disclosure.

FIG. 2 is a flow diagram illustrating a method 200 for analyzing a relationship between one or more agents and one or more clinical outcomes, in accordance with an embodiment of the disclosure. As shown, the method 200 begins at step 202, where a processor, such as a processor associated with the calculation engine 126, receives a selection of an agent. In one embodiment, the agent is a prescription drug. At step 204, the processor receives selection of an adverse event. In some embodiments, adverse events are clinic events. Non-limiting examples include accidents, cancer, congestive heart failure, depression, diarrhea, glaucoma, infection, liver dysfunction, lymphoma, major bleeding, renal failure, seizures, sudden death, suicide, among many others. In some embodiments, the adverse events are coded according to standard external definitions (for example, by the government). In other embodiments, the adverse events are coded according to proprietary definitions. In some embodiments, adverse events can be non-clinical in nature, but rather more "public policy" in nature. Examples include detecting mental health patterns in populations, etc. While such non-clinical adverse events may not be an acute clinical adverse event for a given drug, certain healthcare entities (such as the FDA, for example) may be concerned if populations of people who take a given drug over time demonstrate a propensity to commit crimes, to be violent, to be depressed, to be less employed, etc.

At step 206, the processor analyzes clinical data in a database to determine a number of occurrences of the adverse event when the agent is administered. As described, the clinical data can come from many sources, including demographic data, claims data, procedure codes, diagnostic codes, pharmacy/prescription data, patient-entered data, among others. The processor analyzes the data to identify a number of patients that have exhibited the adverse event when taking the drug for a predetermined minimum amount of time (for example, 6 months).

At step 208, the processor applies one or more filters. The clinical data can be filtered according to certain parameters, such as patient age, gender, demographic info, clinical stratification scores and identified conditions, and whether the use of the drug was "on-label" or "off-label" (i.e., "on-label" refers to use in the recommended or FDA approved manner; "off-label" refers to use in a non-recommended or non-FDA approved manner), among others. The analysis performed at step 206 can, therefore, be applied only to the data that satisfies the filters. In some embodiments, step 208 is performed before step 206. Also, in some embodiments, step 208 is optional and is omitted. In such a case, no filter is applied, and all the clinical data is analyzed.

At step 210, the processor calculates a risk score corresponding to the adverse event and the agent. According to some embodiments, the risk score can be an absolute risk or a relative risk. Table 1 below illustrates occurrences of the adverse event when a particular drug is administered, a total number of patients that suffered the adverse event, a total number of patients to whom the drug was administered, and a total number of patients to whom the drug was not administered.

TABLE 1

|  | Drug | No Drug | Total |
|---|---|---|---|
| Adverse Event | IAO |  | IO |
| No Adverse Event |  |  |  |
| Total | IA |  | I |

In Table 1, "IAO" refers to the occurrence of the adverse event when the drug is administered, "IO" refers to the total number of patients that suffered the adverse event, "IA" refers to the total number of patients to whom the drug was administered, and "I" refers to the total number of patients to whom the drug was not administered.

According to one embodiment, an "ON agent risk," "NO agent risk," "Absolute Risk," and "Relative Risk" can be calculated using Equations 1 to 4, respectively:

$$ONagentRisk = \frac{IAO}{IA}, \quad \text{(Equation 1)}$$

$$NOagentRisk = \frac{IO - IAO}{I - IA}, \quad \text{(Equation 2)}$$

$$AbsoluteRisk = ONagentRisk - NOagentRisk, \text{ and} \quad \text{(Equation 3)}$$

$$RelativeRisk = \frac{ONagentRisk}{NOagentRisk}. \quad \text{(Equation 4)}$$

A "chi-squared" analysis can also be performed to calculate a confidence level for the statistical analysis performed using Equation 5:

$$\chi^2 = \frac{(I)[(IAO)(I - IO - IA + IAO) - (IO - IAO)(IA - IAO)]^2}{(IA)(I - IA)(IO)(I - IO)}. \quad \text{(Equation 5)}$$

In some embodiments, a "Chi-squared value" or "P-value" may be calculated to test the statistical significance of the calculations.

Table 2, below, illustrates an example where the adverse event is congestive heart failure (CHF) and the drug is an ACE inhibitor.

TABLE 2

|  | Drug | No Drug | Total |
|---|---|---|---|
| Adverse Event | 568 |  | 2433 |
| No Adverse Event |  |  |  |
| Total | 179499 |  | 656938 |

As shown, a total of 179499 patients took the drug and 568 experienced the adverse effect. A total of 2433 patients experienced the adverse effect. A total of 656938 patients did not take the drug.

Using the Equations 1-4 above, the relative risk is calculated at 0.81. The Chi-squared value is calculated using Equation 5 as 19.49.

At step 212, the processor determines whether there are more adverse events to analyze for the selected agent/drug. If the processor determines that there are more adverse events to analyze for the selected agent/drug, then the method 200 returns to step 204, described above. If the processor determines that there are no more adverse events to analyze for the selected agent/drug, then the method 200 proceeds to step 214.

At step 214, the processor determines whether there are more agents/drugs to analyze against adverse events. If the processor determines that there are more agents/drugs to analyze, then the method 200 returns to step 202, described above. If the processor determines that there are no more agents/drugs to analyze, then the method 200 proceeds to step 216.

At step 216, the processor outputs results (i.e., risk scores) to a graphical display. In some embodiments, the results may be graphically represented as a "heat map," where a circle corresponds to the average relative risk of the drug-adverse event combination, and where a greater size of the circle corresponds to a greater average relative risk. Examples are provided below in FIGS. 3-9.

Figure 3:
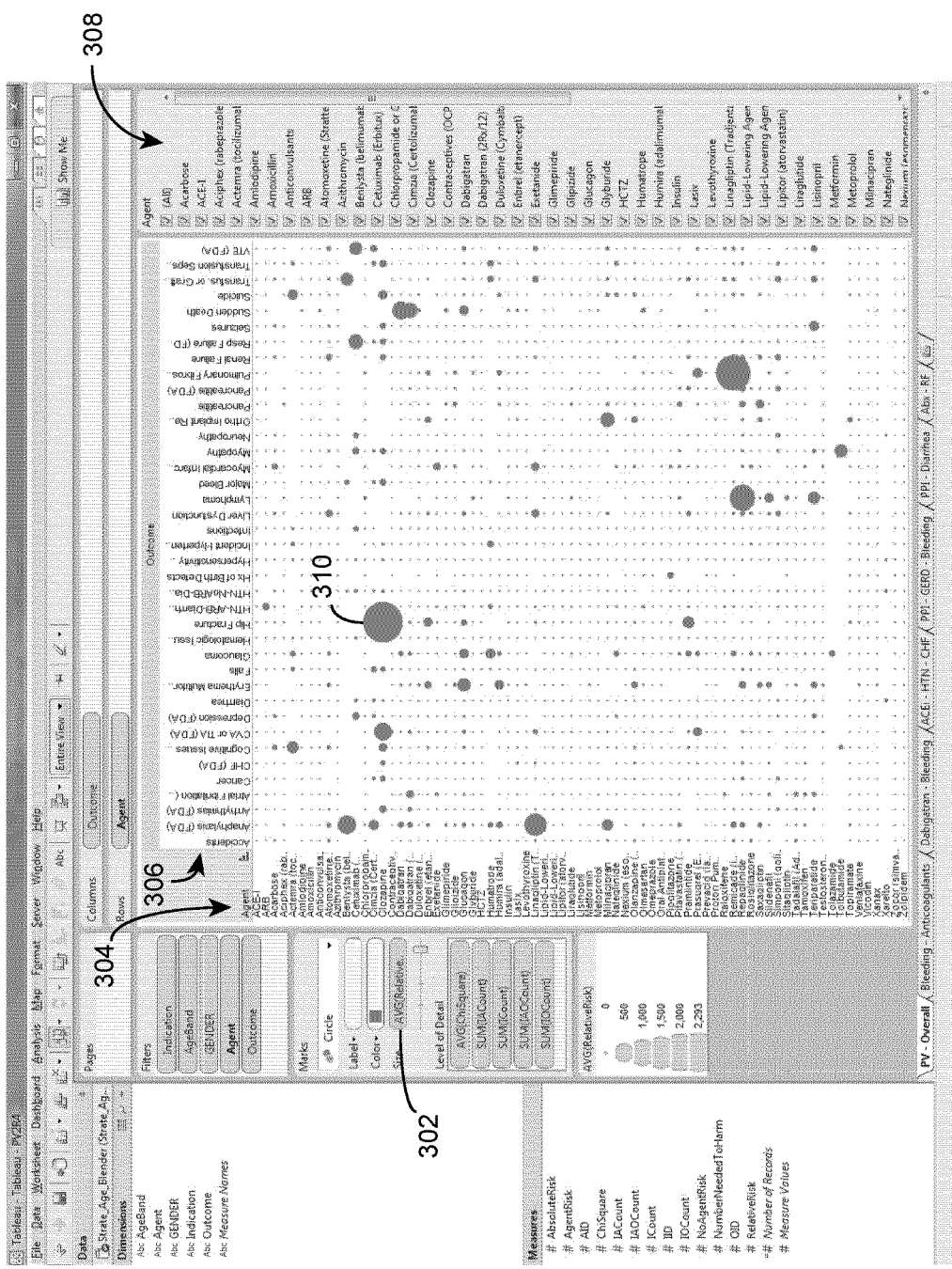
FIG. 3 is a screenshot of a user interface displaying an average relative risk for plurality of agents versus a plurality of outcomes, in accordance with an embodiment of the disclosure.

FIG. 3 is a screenshot of a user interface displaying an average relative risk for plurality of agents versus a plurality of outcomes, in accordance with an embodiment of the disclosure. As shown, a listing of different agents (for example, prescription drugs) is shown along a vertical axis 304 and a listing of different outcomes (for example, adverse clinical events) is shown along a horizontal axis 306. A selection of which agents and/or outcomes are shown in the user interface can be made via interface element 308 via one or more checkboxes. Note, in FIG. 3, the selection of different outcomes is not shown (i.e., a user would need to "scroll down" to see the checkboxes for the different outcomes).

As described above, a processor can calculate a risk score, such as average relative risk, for each combination of agent and outcome. In the example shown in FIG. 3, average relative risk is graphically displayed such that an increase in the size 302 of the circle shown for the particular agent-outcome combination corresponds to an increase in the average relative risk. For example, a high average relative risk is exhibited between the agent "Clozapine" and the outcome "Hip fracture," displayed as circle 310.

Figure 4:
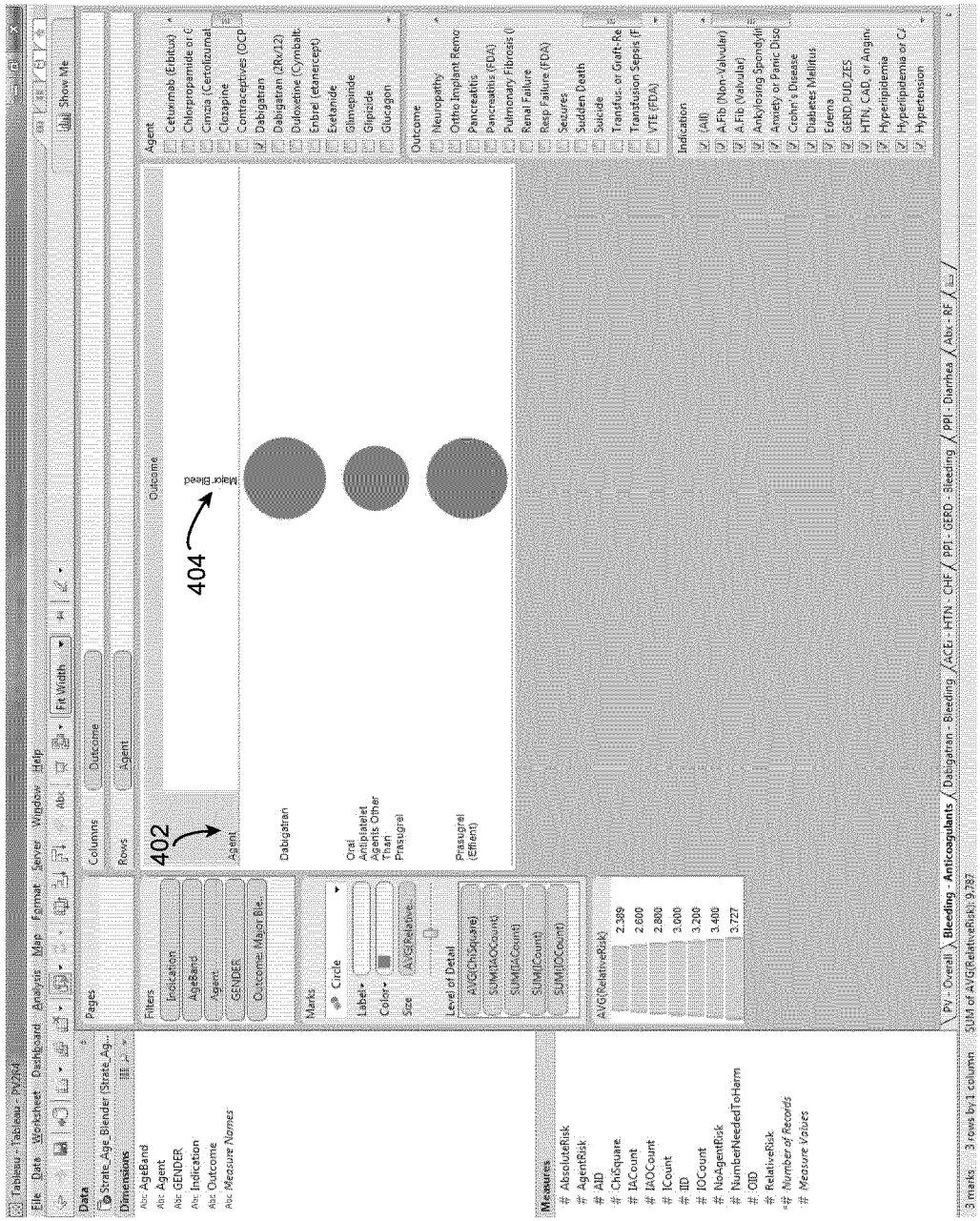
FIG. 4 is a screenshot of a user interface displaying an average relative risk for different agents in the same class of agents relative to a particular outcome, in accordance with an embodiment of the disclosure.

FIG. 4 is a screenshot of a user interface displaying an average relative risk for different agents in the same class of agents relative to a particular outcome, in accordance with an embodiment of the disclosure. In the example shown in FIG. 4, three different blood thinners are shown along a vertical axis 402 relative to a particular outcome (e.g., major bleeding) along a horizontal axis 404. In the example shown, the three blood thinners are "Dabigatran," "Prasugrel," and "oral antiplatelet agents other than Prasugrel." With respect the particular outcome shown, it is readily apparent from the sizes of the circles, that the agent "oral antiplatelet agents other than Prasugrel" has the lowest average relative risk of the three agents. Providing a graphical representation of the average relative risk provides for a superior user experience, when compared to conventional techniques.

Figure 5:
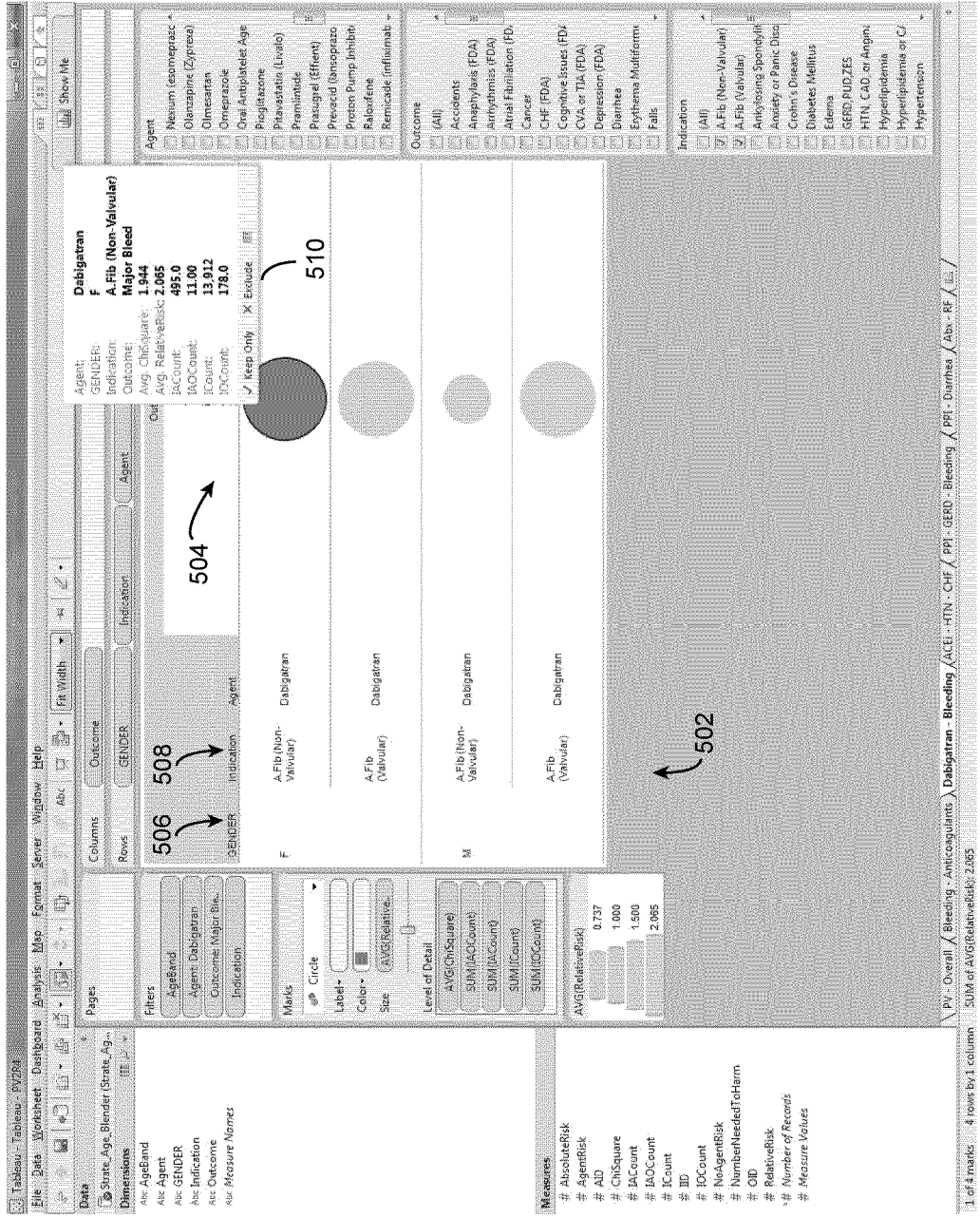
FIG. 5 is a screenshot of a user interface displaying an average relative risk for one agent relative to one outcome, where the data is sorted by one or more filters, in accordance with an embodiment of the disclosure.

FIG. 5 is a screenshot of a user interface displaying an average relative risk for one agent relative to one outcome, where the data is sorted by one or more filters, in accordance with an embodiment of the disclosure. As described, the data can be filtered using one or more filters prior to performing the statistical analysis. In the example shown in FIG. 5, a single outcome (e.g., major bleeding) is shown along a horizontal axis 504. Along the vertical axis 502, a single agent is shown (e.g., "Dabigatran"), where the data is first filtered by gender 506 and then by indication 508. Filtering by "indication," in this example, refers to whether the drug was used in an FDA approved manner (i.e., "on-label") or a non-FDA approved manner (i.e., "off-label"). In the example in FIG. 5, A.Fib "Non-Valvular" refers to the FDA approved mode of administering Dabigatran, and A.Fib "Valvular" refers to the non-FDA approved mode of administering Dabigatran. When comparing the average relative risk for the four different combinations of gender 506 and indication 508, the outcome has a similar average relative risk for both indications (i.e., Non-Valvular and Valvular) for females. However, for males, the Valvular (i.e., non-FDA approved) mode of administering the drug has a significantly greater average relative risk. The outcome shown in FIG. 5 may suggest that a blanket statement from the FDA that prohibits Valvular treatment with Dabigatran (for both males and females) is not necessary, and that the FDA should consider allowing Valvular treatments for women. The results shown using embodiments of the disclosure are not meant to be definitive proof that certain drugs do not cause certain complications/outcomes, but rather to generate a hypothesis for further investigation and/or research.

In addition, in some embodiments, a user can click on or hover a cursor over one of the circles, which causes a dialog box 510 to be displayed. The dialog box 510 includes various counts and statistics for the particular agent-outcome pair.

Figure 6:
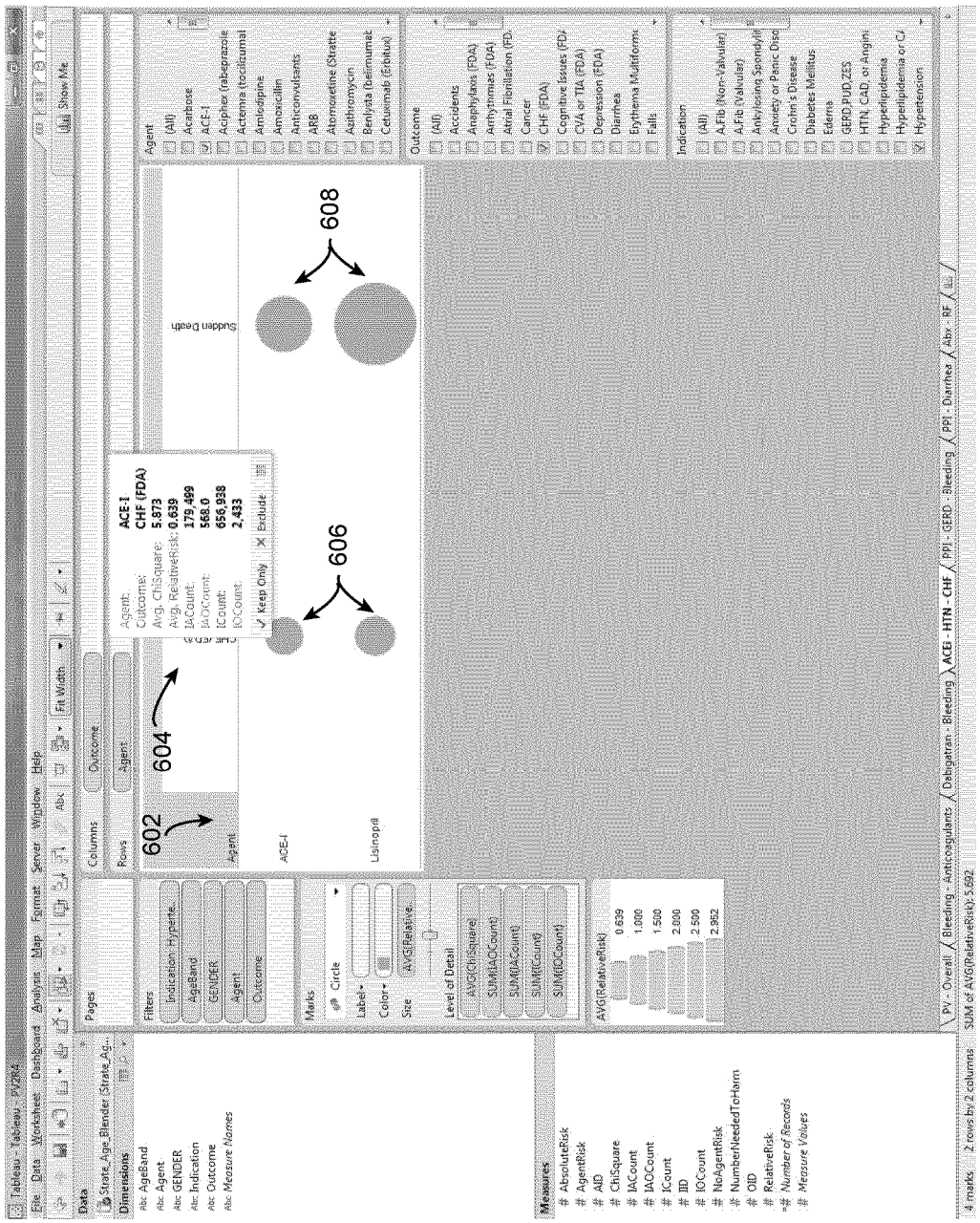
FIGS. 6-8 are screenshots of user interfaces displaying an average relative risk for a plurality of outcomes for one agent relative to other agents in the same class of agents, in accordance with several embodiments of the disclosure.
Figure 7:
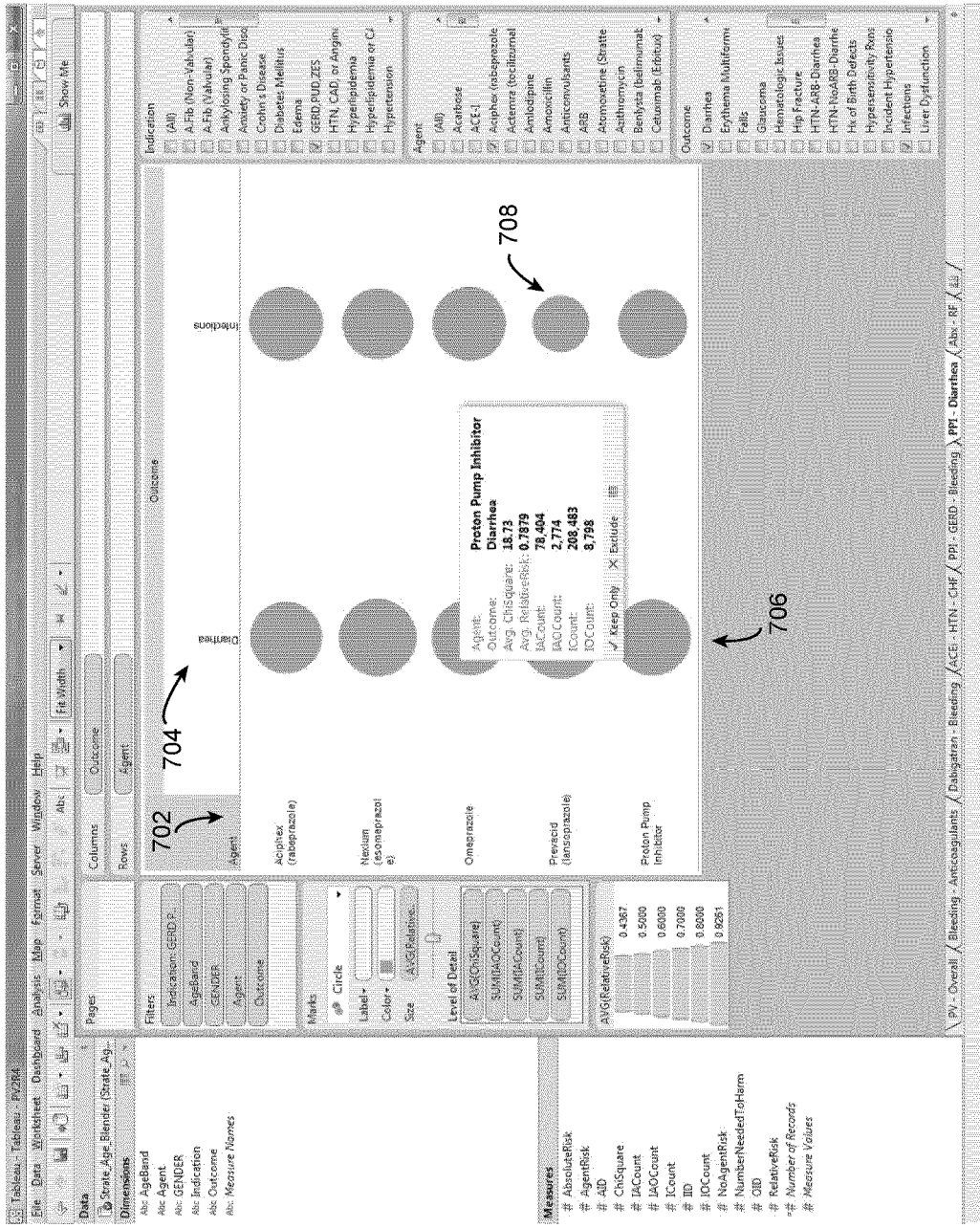
Figure 8:
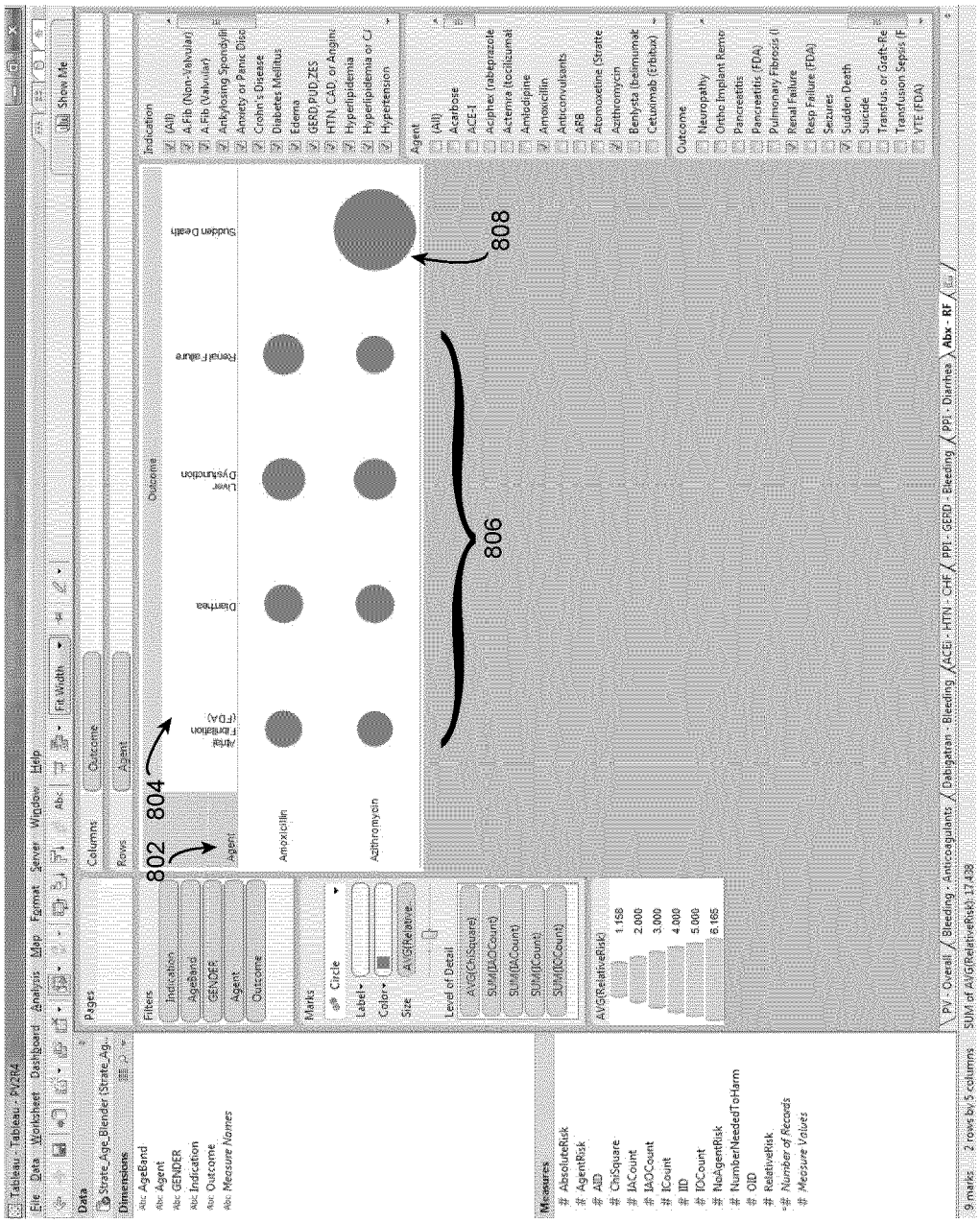

FIGS. 6-8 are screenshots of user interfaces displaying an average relative risk for a plurality of outcomes for one agent relative to other agents in the same class of agents, in accordance with several embodiments of the disclosure.

In FIG. 6, two different outcomes are shown along the horizontal axis 604 (i.e., CHF (congestive heart failure) and sudden death). Along the vertical axis 602, a single agent is shown (i.e., "Lisinopril," an ACE inhibitor) along with an agent grouping (i.e., "ACE-I"), which corresponds to all ACE inhibitors, including the single agent shown separately. As shown in the example in FIG. 6 via circles 606, Lisinopril has a similar average relative risk for CHF as all ACE inhibitors. However, as shown via circles 608, Lisinopril has a higher average relative risk for sudden death compared to all ACE inhibitors. This finding could cause physicians and/or the FDA to place certain warnings on Lisinopril.

In FIG. 7, two different outcomes are shown along the horizontal axis 704 (i.e., diarrhea and infections). Along the vertical axis 702, five different agents from the same class are shown. In this example, five different proton pump inhibitors are shown. As shown in the example in FIG. 7 via circles 706, each of the five proton pump inhibitors has a similar average relative risk for diarrhea. However, with respect to infections, "Prevacid" has a lower average relative risk as compared to the other four proton pump inhibitors, as evidenced by the smaller size of circle 708. As such, in one example, this information tends to show that Prevacid may be superior to the other proton pump inhibitors since the risk for diarrhea is roughly the same as for the other proton pump inhibitors, but with a lower risk for infections.

In FIG. 8, five different outcomes are shown along the horizontal axis 804. Along the vertical axis 802, two different agents from the same class are shown. In this example, two different antibiotics are shown, amoxicillin and azithromycin. As shown in the example in FIG. 8 via circles 806, both antibiotics have similar average relative risk for four of the five outcomes shown. However, with respect to the outcome "sudden death," azithromycin has a relatively large average relative risk (as shown via circle 808) and amoxicillin has a very low (or even calculated "zero") average relative risk for sudden death. Further investigation into this outcome can be performed by applying filters, as shown in FIG. 9.

Figure 9:
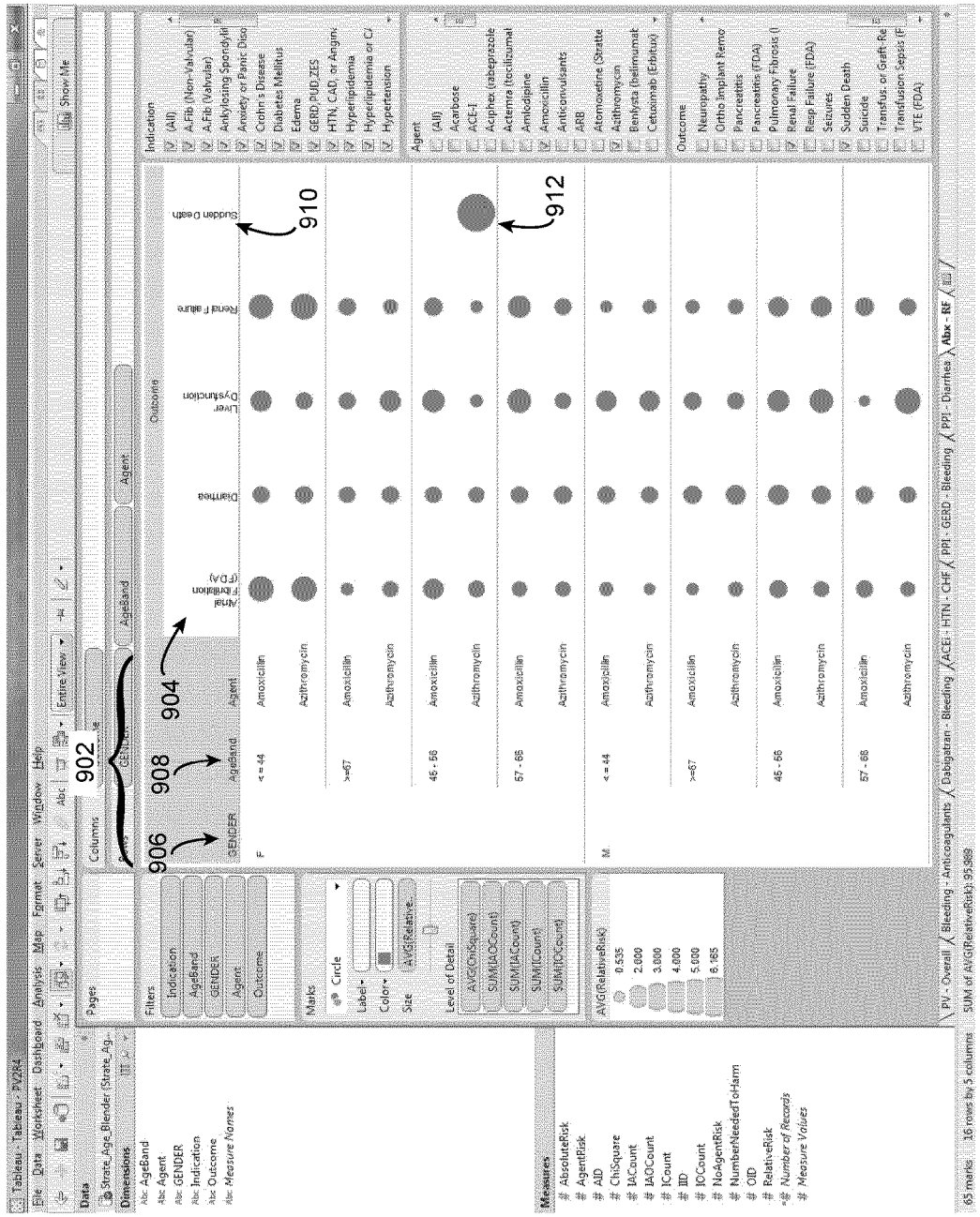
FIG. 9 is a screenshot of a user interface displaying an average relative risk for two agents relative to a plurality of outcomes, where the data is filtered by gender and age, in accordance with an embodiment of the disclosure.

FIG. 9 is a screenshot of a user interface displaying an average relative risk for two agents relative to a plurality of outcomes, where the data is filtered by gender and age, in accordance with an embodiment of the disclosure. In FIG. 9, five different outcomes are shown along the horizontal axis 904. Along the vertical axis 902, two different agents from the same class are shown. In this example, two different antibiotics are shown, amoxicillin and azithromycin. The agents are filtered first by gender 906 and then by age band 908. For the particular outcome in question, "Sudden Death" 910, filtering the data by gender and age band reveals that azithromycin has a relatively high average relative risk for sudden death for women ages 45-56. In one example, the analysis and calculation shown in FIG. 9 may, therefore, "exonerate" azithromycin from the risk of sudden death for all males and for females outside the ages of 45-56.

Figure 10:
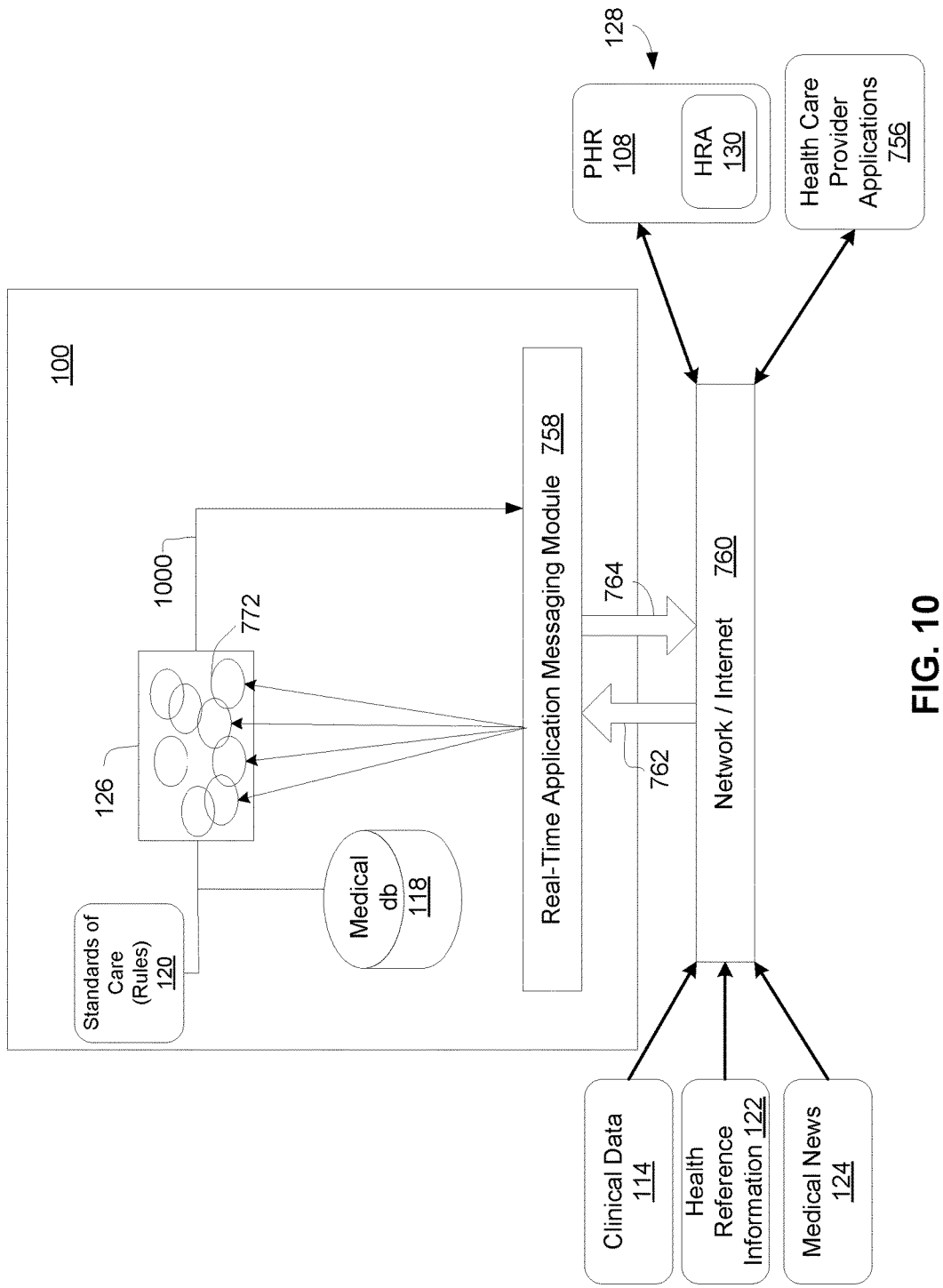
FIG. 10 is a schematic diagram illustrating an overview of a system for analyzing a relationship between one or more agents and one or more clinical outcomes, in accordance with an embodiment of the disclosure.

In the additional embodiment illustrated in FIG. 10, the system and method of the present disclosure implement a plurality of modules for providing real-time processing and delivery of calculated statistics about agents and outcomes. For example, the statistics may be presented to a health care provider 110 via one or more health care provider applications 756. In one implementation, health care organization 100 includes a real-time transfer module 758. The real-time transfer module 758 comprises computer executable instructions encoded on a computer-readable medium, such as a hard drive, of one or more server computers controlled by the health care organization 100. Specifically, the real-time transfer module 758 is configured to calculate statistics, such a risk scores, for real-time information received via a network 760 between the health care organization 100 and external systems and applications. Preferably, the real-time transfer module 758 employs a service-oriented architecture (SOA) by defining and implementing one or more application platform-independent software services to carry real-time data between various systems and applications.

In one embodiment, the real-time transfer module 758 comprises web services 762, 764 that interface with external applications for transporting the real-time data via a Simple Object Access Protocol (SOAP) over HTTP (Hypertext Transfer Protocol). The message ingest web service 762, for example, receives real-time data that is subsequently processed in real-time by the calculation engine 126. The message ingest web service 762 synchronously collects clinical data 114 from the medical insurance carrier 112, patient-entered data 128, including patient-entered clinical data 128, from the patient's PHR 108 and HRA 130, as well as health reference information 122 and medical news information 124. In an embodiment, the message ingest web service 762 also receives clinical data 114 in real-time from one or more health care provider applications 756, such as an electronic medical record (EMR) application and a disease management application. In yet another embodiment, the message ingest service 762 receives at least some of the patient-entered data 128 pursuant to the patient's interaction with a nurse in disease management or an integrated voice response (IVR) system. Incoming real-time data is optionally stored in the medical database 118. Furthermore, incoming real-time data associated with a given patient 102, in conjunction with previously stored data at the database 118 and the clinical rules 120, defines a rules engine run to be processed by the calculation engine 126. Hence, the real-time transfer module 758 collects incoming real-time data from multiple sources and defines a plurality of rules engine runs associated with one or more agents (e.g., drugs) and one or more outcomes (e.g., adverse events) for real-time processing.

The real-time transfer module 758 forwards the rules engine runs to the calculation engine 126 to instantiate a plurality of real-time rule processing sessions 772. The processing of the rule processing sessions 772 by the calculation engine 126 can be load-balanced across multiple logical and physical servers to facilitate multiple and simultaneous requests for real-time calculation of risk scores for one or more pairs of agents and outcomes. In one embodiment, the load-balancing of sessions 772 is accomplished in accordance with a J2EE (Java) specification. Each rule processing session 772 makes calls to the medical database 118 by referring to a unique agent ID field for a corresponding agent (e.g., drug) to receive data related to that agent for processing of incoming real-time data. The results 1000 of the real-time processing of the calculation engine may then be output to the real-time transfer module 758 for distribution to one or more health care provider applications 756 and/or to other servers and/or services via message output service 764.

Figure 11:
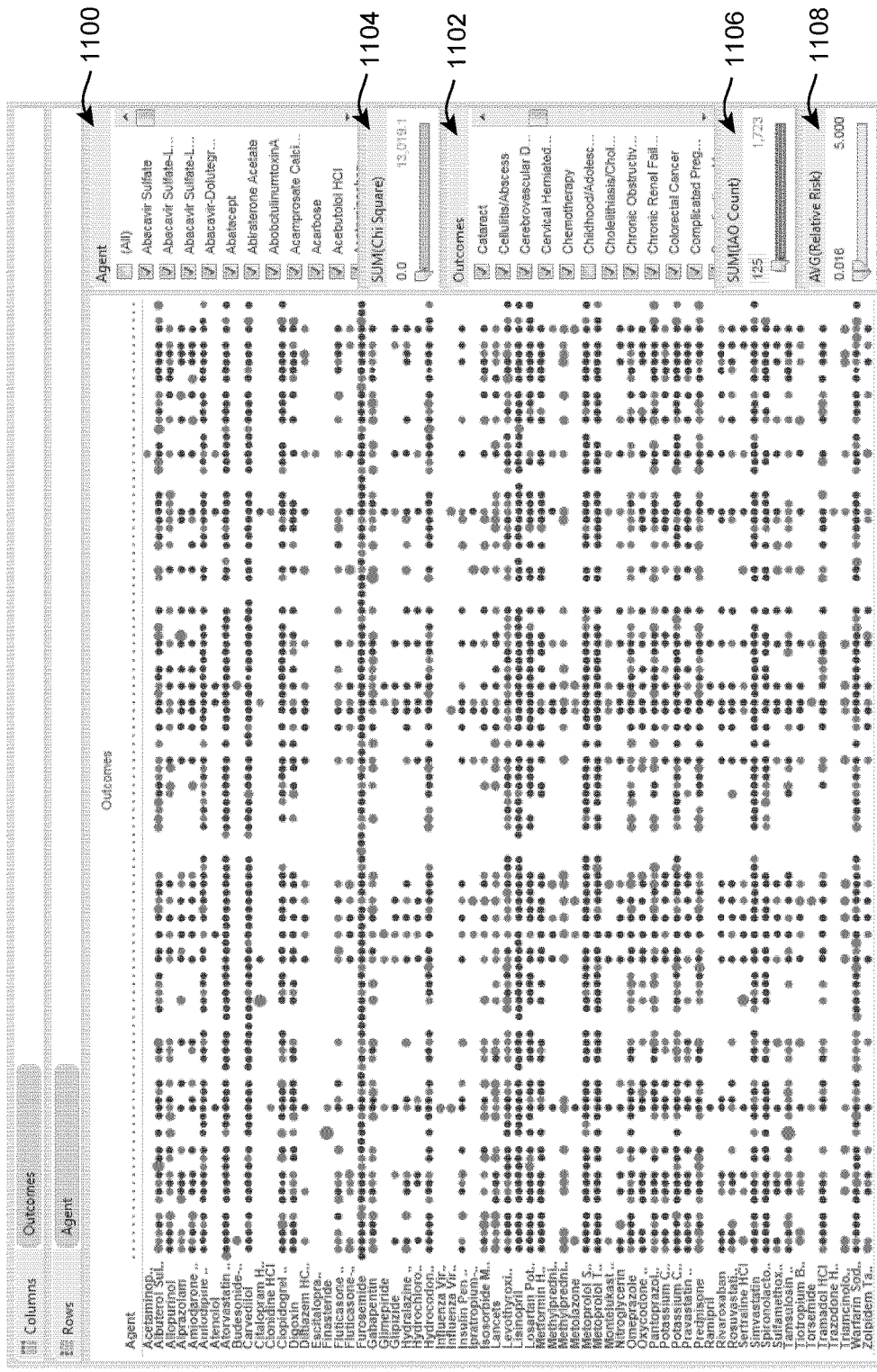
FIG. 11 is a screenshot a of a user interface displaying an average relative risk for a plurality of outcomes for a plurality agents, in accordance with an embodiment of the disclosure.

FIG. 11 is a screenshot a of a user interface displaying an average relative risk for a plurality of outcomes for a plurality agents, in accordance with an embodiment of the disclosure. As shown, the plurality of outcomes is selected via checkboxes 1102 and the plurality agents is selected via checkboxes 1100. In the example shown, the number of agents and outcomes selected is rather large, thus the user interface includes many results. Because of the large number of results, it may be difficult to visually distinguish between the size of the circles that represent the average relative risk for a given combination of agent and outcome.

Thus, embodiments of the disclosure provide user interface elements in the graphical user interface to scale and/or filter the results. As shown, user interface element 1104 may correspond to statistical significance of the data (e.g., Chi-squared or P-value), user interface element 1106 may correspond to count of "IAO," i.e., where the Indication ("I"), Agent ("A"), and Outcome ("O") are each present, and user interface element 1108 may correspond to average relative risk. In some implementations, "statistically significant" results corresponding to the user interface element 1104 may comprise results with a Chi-squared value of five (5.0) or more. In the example shown in FIG. 11, each of the user interface elements 1104, 1106, 1108 includes a slider having adjustable low-end and or high-end thresholds. In other examples, each of the user interface elements 1104, 1106, 1108 may includes only one of a slider for the low-end threshold or the high-end threshold.

A user may interact with one or more of the user interface elements 1104, 1106, 1108 to filter the data in an effort to reduce the number of agent-outcome results shown in the user interface. In the example in FIG. 11, the low-end threshold for user interface element 1106 corresponding to count of "IAO" is set to "125."

Figure 12:
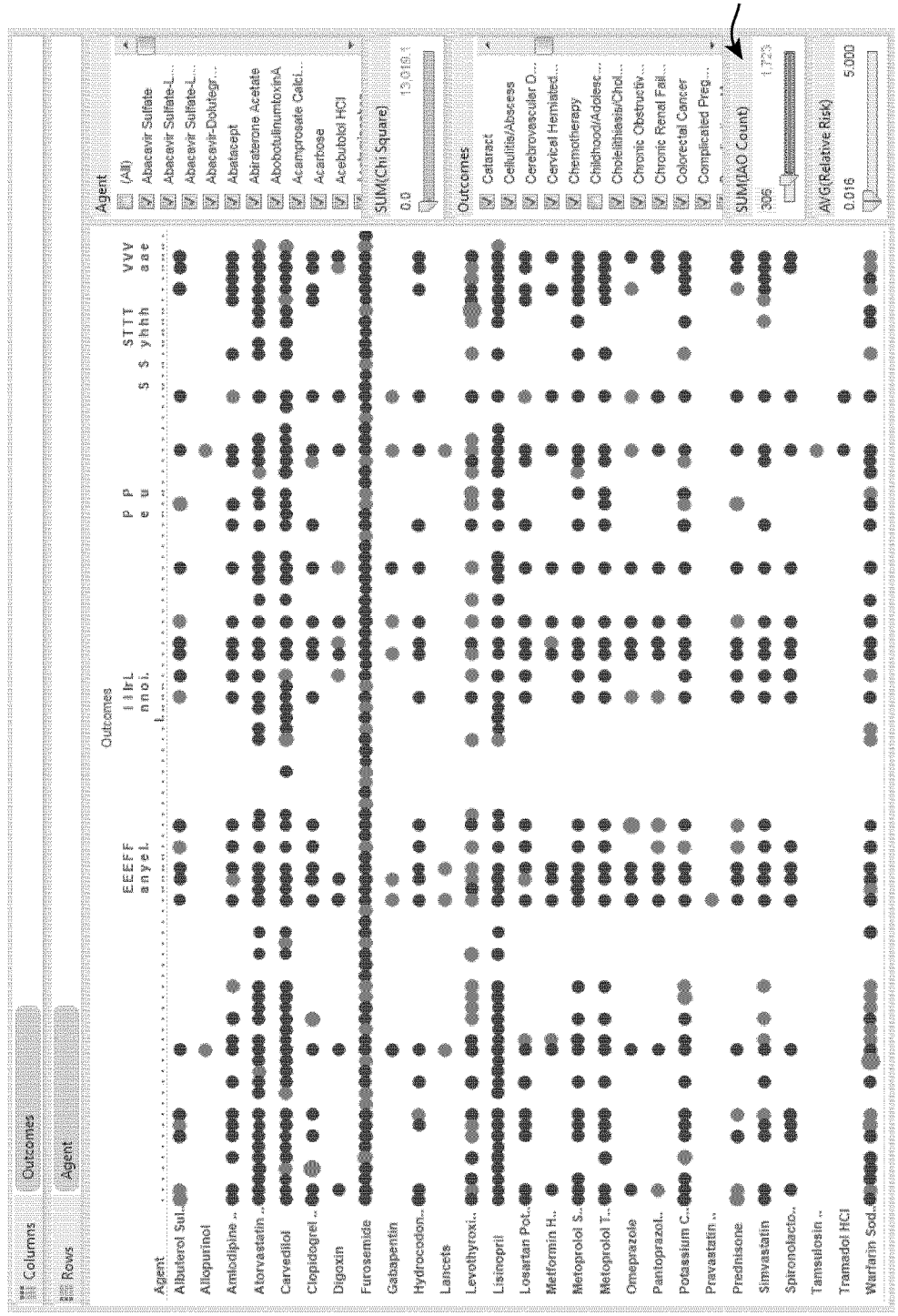
FIG. 12 is a screenshot a of a user interface displaying an average relative risk for a plurality of outcomes for a plurality agents, where scaling and filtering of the results is applied, in accordance with an embodiment of the disclosure.

FIG. 12 is a screenshot a of a user interface displaying an average relative risk for a plurality of outcomes for a plurality agents, where scaling and filtering of the results is applied, in accordance with an embodiment of the disclosure. As shown, in FIG. 12, the low-end threshold for user interface element 1106 corresponding to count of "IAO" is increased to 306 (i.e., from "125" shown in FIG. 11). This causes the user interface to display fewer agent-outcome pairings because fewer agent-outcome pairings satisfy the updated low-end threshold for user interface element 1106 corresponding to count of "IAO." Since there are fewer signals that satisfy the criteria, fewer agent-outcome pairings are displayed in the user interface, which increases the readability and usefulness of the user interface.

Figure 13:
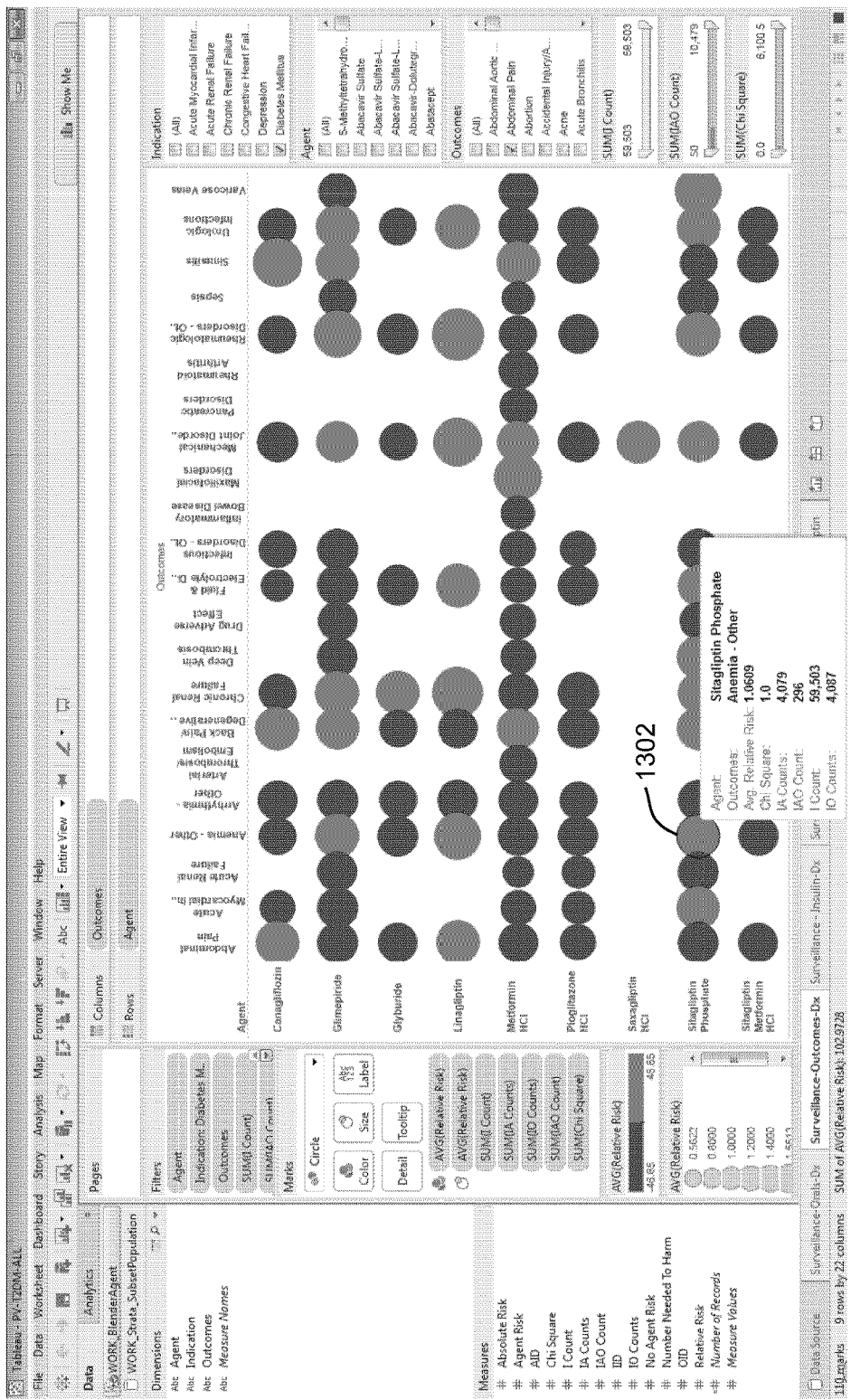
FIGS. 13-14 are screenshots user interfaces displaying an average relative risk for a plurality of outcomes for a plurality agents, in accordance with embodiments of the disclosure.

FIG. 13 is a screenshot a of a user interface displaying an average relative risk for a plurality of outcomes for a plurality agents, in accordance with an embodiment of the disclosure. The Indication ("I") in the example in FIG. 13 is "Diabetes Mellitus." In some implementations, an average relative risk of greater than "1.0" indicates that for patients having the Indication, the given Agent is "harmful," in that it is associated with a greater risk of leading to the Outcome. On the other hand, an average relative risk less than "1.0" indicates that for patients having the Indication, the given Agent is "protective," in that it is associated with a lower risk of leading to the Outcome.

As described herein, a plurality of agents can be analyzed against a plurality of outcomes. In FIG. 13, an example agent-outcome combination 1302 (i.e., corresponding to agent "Sitagliptin Phosphate" and outcome "Anemia—Other") is examined. The example agent-outcome combination 1302 has an average relative risk greater than "1.0," i.e., "1.0609." A relative risk greater than 1.0 suggests that for patients having the Indication, the given Agent is "harmful" in that it is associated with a greater risk of leading to the Outcome. However, as shown in FIG. 14, this result can be further stratified/categorized and analyzed for more information.

Figure 14:
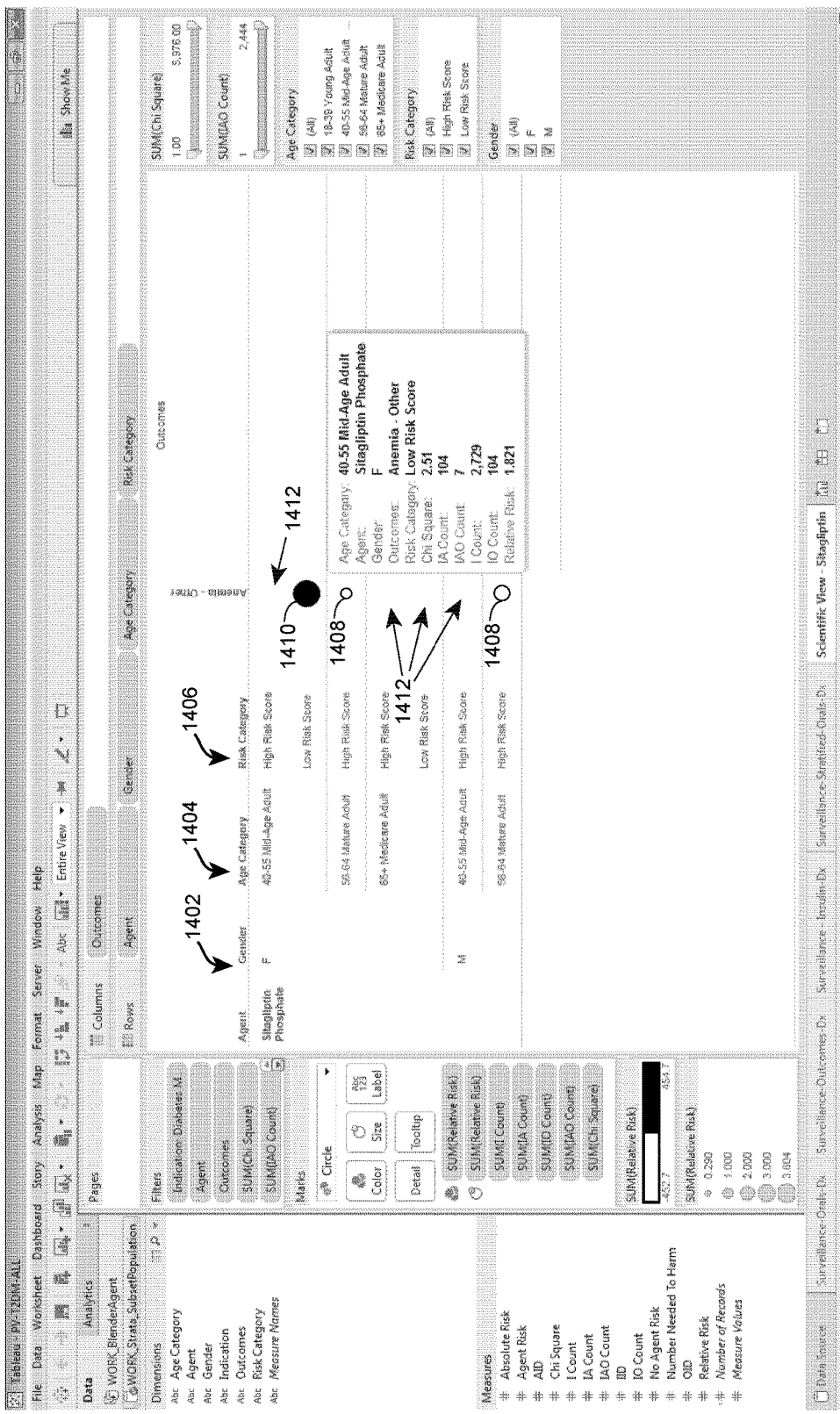

FIG. 14 is a screenshot a of user interface displaying an average relative risk for a plurality of outcomes for a plurality agents where patients are stratified, in accordance with an embodiment of the disclosure. The example agent-outcome combination 1302 from FIG. 13 corresponding to "Sitagliptin Phosphate" and "Anemia—Other" is examined in detail. For example, a user may double-click on circle corresponding to the example agent-outcome combination 1302 in FIG. 13 to cause the user interface in FIG. 14 to be displayed.

As shown in FIG. 14, the patients are stratified according to their characteristics based on gender 1402, age 1404, and risk category 1406. In one example, risk categories 1406 include "low" risk or "high" risk, based on a patient's given medical and personal information. The stratifications shown in FIG. 14 are merely examples, and other stratifications are also with the scope of the disclosure. For example, patients can be stratified by geographical region (e.g., state), by income ranges, or any other metric.

In the example shown in FIG. 14, the relative risk for a given stratification for the agent-outcome pairing is shown as a white circle 1308 when the average relative risk is below "1.0," i.e., the agent is "protective" relative to the outcome for that stratification. The relative risk for a given stratification for the agent-outcome pairing is shown as a black circle 1310 when the average relative risk is greater than "1.0," i.e., the agent is "harmful" relative to the outcome for that stratification. A larger black circle represents a greater relative risk, i.e., more harmful. A larger white circle represents a lower relative risk, i.e., more protective. The choice of whether the harmful/protective circles get larger or smaller as a function of being more harmful/protective is matter of design choice.

In the example in FIG. 14, where there is no circle for a given stratification (i.e., locations 1312 in FIG. 14), then the agent is shown to have no impact relative to the outcome.

Further, as shown in FIG. 14, some stratifications have no data. In the example shown, a patient's gender 1402 can be Male, Female, or Unknown. A patient's age categories 1404 may be: 15 years old or under, 16-39 years old, 40-55 years old, 56-64 years old, or 65+ years old. A patient's risk category 1406 may be Low or High risk. In the example shown, certain combinations of gender 1402, age 1404, and risk category 1406 have no results in the table shown in the user interface. For example, for Males, there is only displayed categories for 40-55 years old with High risk and 56-64 years with High risk. None of the Male's "Low risk" age categories are shown. This means that for the certain combinations of categories/stratifications not shown, there are no patients with that satisfy those particular categories/stratifications and exhibit all three of: (a) the Indication (e.g., "Diabetes Mellitus"), (b) the Agent (e.g., "Sitagliptin Phosphate"), and (c) the Outcome (e.g., "Anemia—Other").

Based on the stratified data shown in FIG. 14, a processor is able to automatically vilify and/or exonerate certain agents from influencing certain outcomes for specific stratifications/categories of people. The processor may "vilify" an agent by determining that, for a population with a given Indication (e.g., disease), if the average relative risk of a given outcome for a specific stratification of people when a given agent is administered is above 1.0, then the agent is harmful for that specific stratification of patients relative to that outcome (e.g., the black circles 1410 in FIG. 14). In the reverse direction, the processor may "exonerate" an agent by determining that, for a population with a given Indication (e.g., disease), if the average relative risk of a given outcome for a specific stratification of people when a given agent is administered is less than 1.0, then the agent is protective for that specific stratification of patients relative to that outcome (e.g., the white circles 1408 in FIG. 14). In addition, the processor may further "exonerate" an agent by determining that there is no circle for that agent-outcome pairing for a particular stratification of patients (i.e., locations 1412).

In some embodiments, when an agent has been determined to be harmful, the processor may further send a notification to one or more entities to inform them of this potential risk. For example, the processor may notify the FDA (Food and Drug Administration), the public (e.g., label warning updates), product liability insurers, and/or individual patient patients. In some embodiments, notices may be sent directly to registered patient devices (e.g., smart phones, etc.). In some embodiments, reporting on information may be helpful to drug manufacturers or health plan organizations for: performing second-level confirmatory analytics, in reapplying for additional off-label uses (e.g., different patient populations (e.g., by gender, ethnicity, age band, etc.), in exonerating a drug for broader use within the population (e.g., by narrowing the risk to particular genders, ethnicity, age bands, etc.), in applying for an unanticipated use (e.g., where an unanticipated benefit or harm has been identified), for re-pricing (e.g., reports can be used by health plans to inform negotiations for "value based" pricing of drugs; can inform drug manufacturers on higher value for drugs with new/expanded uses), for refining criteria for plan benefit eligibility, and for remarketing a drug, among other uses. In some embodiments, the notification is sent only if the agent-outcome pairing indicates a relative risk greater than 1, but also greater than a certain threshold.

Figure 15:
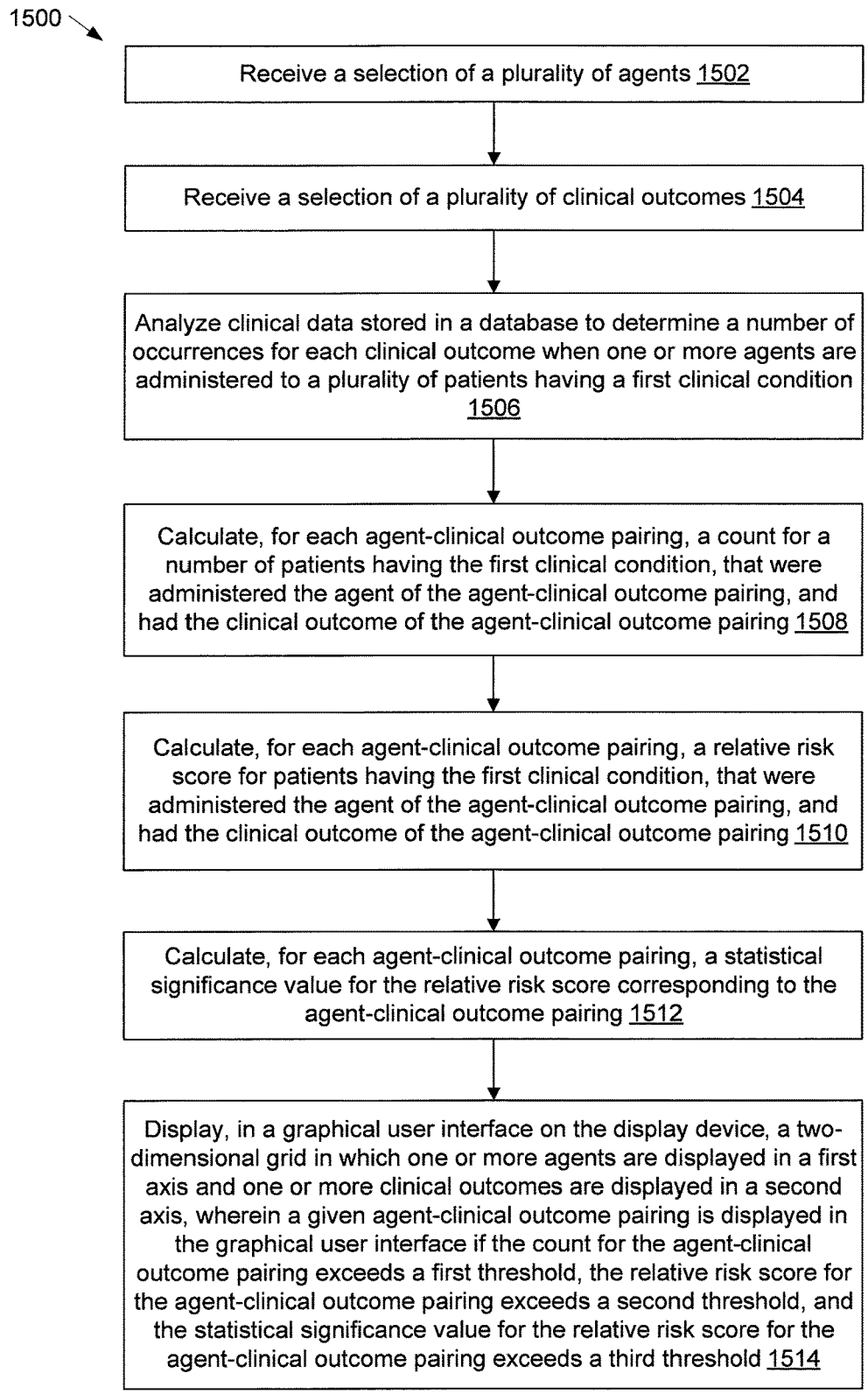
FIG. 15 is a flow diagram of a method for displaying a graphical representation of relationships between a plurality of agents and a plurality of clinical outcomes.

FIG. 15 is a flow diagram of a method for displaying a graphical representation of relationships between a plurality of agents and a plurality of clinical outcomes. As shown, the method 1500 begins at step 1502, where a processor, such a processor that executes the calculation engine 126, receives a selection of a plurality of agents. At step 1504, the processor receives a selection of a plurality of clinical outcomes.

At step 1506, the processor analyzes clinical data stored in a database to determine a number of occurrences for each clinical outcome when one or more agents are administered to a plurality of patients having a first clinical condition. The clinical data stored in the database may include demographic data, lab data, pharmacy data, claims data, diagnostic codes, procedure codes, heath reference information, medical news, standards-of-care, and/or patient-entered data.

At step 1508, the processor calculates, for each agent-clinical outcome pairing, a count for a number of patients having the first clinical condition, that were administered the agent of the agent-clinical outcome pairing, and had the clinical outcome of the agent-clinical outcome pairing. At step 1510, the processor calculates, for each agent-clinical outcome pairing, a relative risk score for patients having the first clinical condition, that were administered the agent of the agent-clinical outcome pairing, and had the clinical outcome of the agent-clinical outcome pairing. At step 1512, the processor calculates, for each agent-clinical outcome pairing, a statistical significance value for the relative risk score corresponding to the agent-clinical outcome pairing. Calculating the statistical significance value comprises calculating one or more of a Chi-squared value and a P-value.

At step 1514, the processor displays, in a graphical user interface on the display device, a two-dimensional grid in which one or more agents are displayed in a first axis and one or more clinical outcomes are displayed in a second axis, where a given agent-clinical outcome pairing is displayed in the graphical user interface if the count for the agent-clinical outcome pairing exceeds a first threshold, the relative risk score for the agent-clinical outcome pairing exceeds a second threshold, and the statistical significance value for the relative risk score for the agent-clinical outcome pairing exceeds a third threshold.

The graphical user interface may further include a first slider graphical user interface element corresponding to the first threshold value, where adjusting the first slider causes the first threshold value to be adjusted. The graphical user interface may further include a second slider graphical user interface element corresponding to the second threshold value, wherein adjusting the second slider causes the second threshold value to be adjusted. The graphical user interface may further include a third slider graphical user interface element corresponding to the third threshold value, wherein adjusting the third slider causes the third threshold value to be adjusted.

Figure 16:
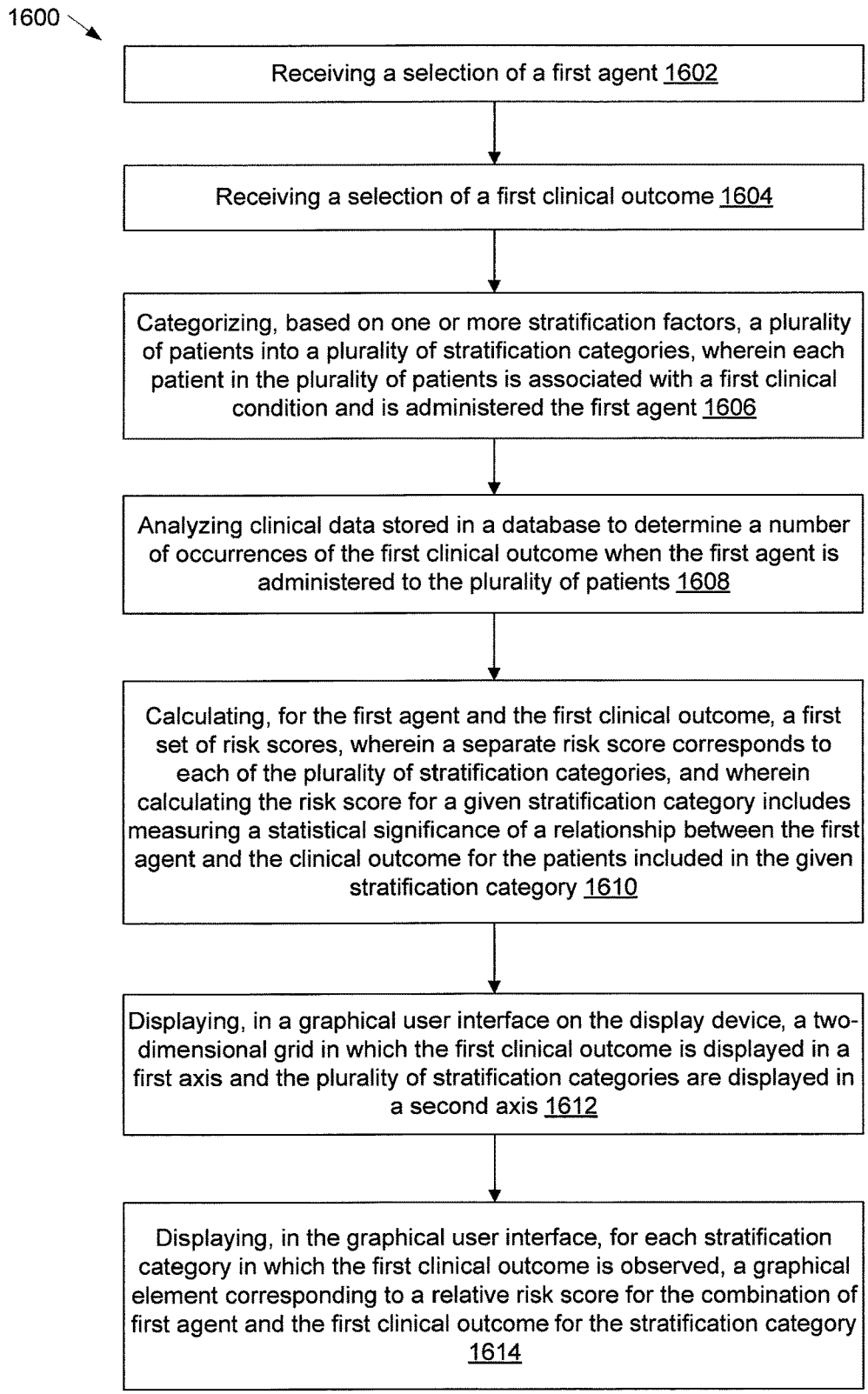
FIG. 16 is a flow diagram of a method for analyzing a relationship between an agent and a clinical outcome.

FIG. 16 is a flow diagram of a method for analyzing a relationship between an agent and a clinical outcome. As shown, the method 1600 begins at step 1602, where a processor, such a processor that executes the calculation engine 126, receives a selection of a first agent. At step 1604, the processor receives a selection of a first clinical outcome.

At step 1606, the processor categorizes, based on one or more stratification factors, a plurality of patients into a plurality of stratification categories, wherein each patient in the plurality of patients is associated with a first clinical condition and is administered the first agent. In some embodiments, the one or more stratification factors include one or more of: a gender stratification factor, an age category stratification factor, a risk category stratification factor, and a geographic location stratification factor.

At step 1608, the processor analyzes clinical data stored in a database to determine a number of occurrences of the first clinical outcome when the first agent is administered to the plurality of patients. At step 1610, the processor calculates, for the first agent and the first clinical outcome, a first set of risk scores, wherein a separate risk score corresponds to each of the plurality of stratification categories, and wherein calculating the risk score for a given stratification category includes measuring a statistical significance of a relationship between the first agent and the clinical outcome for the patients included in the given stratification category.

At step 1612, the processor displays, in a graphical user interface on the display device, a two-dimensional grid in which the first clinical outcome is displayed in a first axis and the plurality of stratification categories are displayed in a second axis.

At step 1614, the processor displays, in the graphical user interface, for each stratification category in which the first clinical outcome is observed, a graphical element corresponding to a relative risk score for the combination of first agent and the first clinical outcome for the stratification category. In one embodiment, a relative risk score less than 1.0 is displayed in a first color, and a relative risk score greater than 1.0 is displayed in a second color. In some embodiments, each graphical element displayed in the graphical user interface comprises a circle, where for a relative risk greater than 1.0 a larger circle corresponds to a greater relative risk.

In some embodiments, based on determining that the first relative risk score is less than 1.0 and less than a first threshold value, the processor determines that the first agent is protective with respect to the first clinical outcome for patients in the first stratification category and associated with the first clinical condition. In some embodiments, based on determining that the first relative risk score is greater than 1.0 and greater than the first threshold value, the processor determines that the first agent is harmful with respect to the first clinical outcome for patients in the first stratification category and associated with the first clinical condition. In some embodiments, based on determining that the first clinical outcome is not observed, the processor determines that the first agent is exonerated from causing the first clinical outcome for patients in the first stratification category and associated with the first clinical condition. In some embodiments, absence of a first stratification category in the second axis corresponds to the first clinical outcome not being observed for the patients administered the first agent in the first stratification category.

In sum, embodiments described herein provide a system and method for pharmacovigilance, i.e., drug surveillance. The systems and methods described herein may, in some implementations, be used by drug companies or others (such as, for example, the FDA) to monitor and test the safety and efficacy of drugs with respect to certain outcomes. The systems and methods could be customized by applying certain filters to analyze the data at finer granularity.

Some embodiments compute the clinical context of a health outcome or adverse event, rather than simply pairing a drug to a health outcome of interest. In various implementations, this includes analyzing the existence of an FDA-labeled indication for the drug (i.e., on-label use versus off-label use), the relative frequency of the symptoms for the outcome of interest (e.g., dizziness or palpitations may be symptoms of an arrhythmia), the relative frequency of testing for the outcome of interest (e.g., Holter EKG monitoring may be used to detect arrhythmias) to calibrate whether frequency of the outcome of interest (e.g., there may appear to be more liver abnormalities just because more liver function testing was being done), the relative frequency of the outcome itself, and the relative frequency of "rescue treatments" related to the outcome, e.g. for a drug that causes diarrhea, the frequency of anti-diarrheal treatments (as opposed to episodes of the diarrhea itself).

Embodiments aggregate this data in a manner not only to detect new signals of drug-adverse event relationships, but can be configured in a way to "exonerate" drugs or confirm drug effects by providing data to suggest that (i) no agent-outcome relationships were detected, (ii) limited agent-outcome relationships were detected (e.g., in a subset of a population previously believed to be at risk of a negative effect), or (iii) a previous agent-outcome relationship is affirmed. Data resulting from such a determination may be used in assessing liability associated with the manufacture, marketing and/or sale of pharmaceuticals. In this way, drugs that may appear to be generating signals in the FDA AERS (Adverse Event Reporting System) may be compared against the signal confirmation versus exoneration findings calculated using embodiments of the disclosure. For example, using the embodiments disclosed herein, which are capable of updating on a near-real-time basis by running analysis on a frequent repeated basis (e.g., weekly, monthly), signals are detected earlier and trend analysis for emerging and/or fading signals can be performed more quickly.

In another embodiment, adverse events or benefits associated with a given drug may be detected across multiple related individuals including teratogenic effects on children. For example, where a mother takes a given drug during pregnancy, the child may be exposed to and suffer consequences during fetal development, with observable long-term consequences which can be detected through the present invention.

In another embodiment, an association between an event and an agent or intervention may be evaluated to determine if a causal relationship among the two potentially exists (or, if the association is a spurious correlation) by evaluating healthcare claim data to determine the sequential relationship between the event and the agent.

All references, including publications, patent applications and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A method for analyzing a relationship between an agent and a clinical outcome, the method comprising:
    categorizing, by a processor and based on one or more stratification factors, a plurality of patients into a plurality of stratification categories, wherein each patient in the plurality of patients is associated with a first clinical condition and is administered a first agent;

analyzing, by the processor, clinical data stored in a database to determine a number of occurrences of each clinical outcome in a plurality of clinical outcomes when the first agent is administered to the plurality of patients;

calculating, by the processor, for the first agent and a first clinical outcome in the plurality of clinical outcomes, an overall risk score corresponding to the first clinical outcome for the plurality of patients;

displaying, on a display device in a first graphical user interface, the overall risk score corresponding to the first clinical outcome as a user interface element;

receiving a selection of the user interface element;

calculating, by the processor, for the first agent and the first clinical outcome, a first set of risk scores, wherein each risk score in the first set of risk scores corresponds to a risk score for a particular stratification category included in the plurality of stratification categories, and wherein calculating the risk score for a given stratification category includes measuring a statistical significance of a relationship between the first agent and the first clinical outcome for the patients included in the given stratification category;

displaying, in response to the selection and on the display device in a second graphical user interface, a two-dimensional grid in which the first clinical outcome is displayed in a first axis and the plurality of stratification categories are displayed in a second axis; and displaying, in response to the selection and on the display device in the second graphical user interface, for each stratification category in which the first clinical outcome is observed, a graphical element in the two-dimensional grid for a corresponding risk score in the first set of risk scores for the combination of first agent and the first clinical outcome for the stratification category.

2. The method of claim 1, wherein the corresponding risk score is displayed in a first color when the corresponding risk score is less than 1.0, and the corresponding risk score is displayed in a second color when the corresponding risk score is greater than 1.0.

3. The method of claim 1, further comprising:
determining, by the processor, that a first relative risk score for a first stratification category is less than 1.0;
determining, by the processor, that the first relative risk score is also less than a first threshold value; and
based on determining that the first relative risk score is less than 1.0 and less than the first threshold value, determining, by the processor, that the first agent is protective with respect to the first clinical outcome for patients in the first stratification category and associated with the first clinical condition.

4. The method of claim 1, further comprising:
determining that a first relative risk score for a first stratification category is greater than 1.0;
determining that the first relative risk score is also greater than a first threshold value; and
based on determining that the first relative risk score is greater than 1.0 and greater than the first threshold value, determining that the first agent is harmful with respect to the first clinical outcome for patients in the first stratification category and associated with the first clinical condition.

5. The method of claim 1, further comprising:
determining, by the processor, that the first clinical outcome is not observed for patients in a first stratification category in which the first agent is administered; and based on determining that the first clinical outcome is not observed, determining, by the processor, that the first agent is exonerated from causing the first clinical outcome for patients in the first stratification category and associated with the first clinical condition.

6. The method of claim 1, wherein absence of a first stratification category in the second axis corresponds to the first clinical outcome not being observed for the patients administered the first agent in the first stratification category.

7. The method of claim 1, wherein calculating the first set of risk scores is based on a total number of patients in an entire population, a number of patients to whom the first agent is administered, a number of occurrences of the first clinical outcome when the first agent is administered, and a total number of patients in the entire population that experienced the first clinical outcome.

8. The method of claim 1, wherein the one or more stratification factors include a gender stratification factor.

9. The method of claim 8, wherein the one or more stratification factors further include one or more of: an age category stratification factor, a risk category stratification factor, and a geographic location stratification factor.

10. The method of claim 1, wherein each graphical element in the two-dimensional grid displayed in the second graphical user interface comprises a circle, wherein a size of each circle is correlated to a relative risk, and wherein the size of the circle is increased when the relative risk is greater than 1.0 and the size of the circle is decreased when the relative risk is less than 1.0 wherein for a relative risk greater than 1.0 a larger circle corresponds to a greater relative risk.

11. A non-transitory computer-readable storage medium storing instructions that when executed by a processor cause a computer system to analyze a relationship between an agent and a clinical outcome, by performing the steps of:
categorizing, based on one or more stratification factors, a plurality of patients into a plurality of stratification categories, wherein each patient in the plurality of patients is associated with a first clinical condition and is administered a first agent;
analyzing clinical data stored in a database to determine a number of occurrences of each clinical outcome in a plurality of clinical outcomes when the first agent is administered to the plurality of patients;
calculating for the first agent and a first clinical outcome in the plurality of outcomes, an overall risk score corresponding to the first clinical outcome for the plurality of patients;
displaying, on a display device in a first graphical user interface, the overall risk score corresponding to the first clinical outcome as a user interface element;
receiving a selection of the user interface element;
calculating, for the first agent and the first clinical outcome, a first set of risk scores, wherein each risk score in the first set of risk scores corresponds to a risk score for a particular stratification category included in the plurality of stratification categories, and wherein calculating the risk score for a given stratification category includes measuring a statistical significance of a relationship between the first agent and the first clinical outcome for the patients included in the given stratification category;
displaying, in response to the selection and on the display device in a second graphical user interface, a two-dimensional grid in which the first clinical outcome is displayed in a first axis and the plurality of stratification categories are displayed in a second axis; and displaying, in response to the selection and on the display device in the second graphical user interface, for each stratification category in which the first clinical outcome is observed, a graphical element in the two-dimensional grid for a corresponding risk score in the first set of risk scores for the combination of first agent and the first clinical outcome for the stratification category.

12. The computer-readable storage medium of claim 11, wherein the corresponding risk score is displayed in a first color when the corresponding risk score is less than 1.0, and the corresponding risk score is displayed in a second color when the corresponding risk score is greater than 1.

13. The computer-readable storage medium of claim 11, further comprising:
    determining, by the processor, that a first relative risk score for a first stratification category is less than 1.0;
    determining, by the processor, that the first relative risk score is also less than a first threshold value; and
    based on determining that the first relative risk score is less than 1.0 and less than the first threshold value, determining, by the processor, that the first agent is protective with respect to the first clinical outcome for patients in the first stratification category and associated with the first clinical condition.

14. The computer-readable storage medium of claim 11, further comprising:
    determining that a first relative risk score for a first stratification category is greater than 1.0;
    determining that the first relative risk score is also greater than a first threshold value; and
    based on determining that the first relative risk score is greater than 1.0 and greater than the first threshold value, determining that the first agent is harmful with respect to the first clinical outcome for patients in the first stratification category and associated with the first clinical condition.

15. The computer-readable storage medium of claim 11, further comprising:
    determining, by the processor, that the first clinical outcome is not observed for patients in a first stratification category in which the first agent is administered; and
    based on determining that the first clinical outcome is not observed, determining, by the processor, that the first agent is exonerated from causing the first clinical outcome for patients in the first stratification category and associated with the first clinical condition.

16. The computer-readable storage medium of claim 11, wherein absence of a first stratification category in the second axis corresponds to the first clinical outcome not being observed for the patients administered the first agent in the first stratification category.

17. The computer-readable storage medium of claim 11, wherein calculating the first set of risk scores is based on a total number of patients in an entire population, a number of patients to whom the first agent is administered, a number of occurrences of the first clinical outcome when the first agent is administered, and a total number of patients in the entire population that experienced the first clinical outcome.

18. The computer-readable storage medium of claim 11, wherein the one or more stratification factors further include one or more of: a gender stratification factor, an age category stratification factor, a risk category stratification factor, and a geographic location stratification factor.

19. The computer-readable storage medium of claim 11, wherein each graphical element in the two-dimensional grid displayed in the second graphical user interface comprises a circle, wherein a size of each circle is correlated to a relative risk, and wherein the size of the circle is increased when the relative risk is greater than 1.0 and the size of the circle is decreased when the relative risk is less than 1.0.

20. A system comprising:
    a clinical data database; and
    a healthcare organization computing device executing one or more processors to analyze a relationship between an agent and a clinical outcome, by performing the steps of:
        categorizing, based on one or more stratification factors, a plurality of patients into a plurality of stratification categories, wherein each patient in the plurality of patients is associated with a first clinical condition and is administered a first agent;
        analyzing clinical data stored in a database to determine a number of occurrences of each clinical outcome in a plurality of clinical outcomes when the first agent is administered to the plurality of patients;
        calculating for the first agent and a first clinical outcome in the plurality of clinical outcomes, an overall risk score corresponding to the first clinical outcome for the plurality of patients;
        displaying, on a display device in a first graphical user interface, the overall risk score corresponding to the first clinical outcome as a user interface element;
        receiving a selection of the user interface element;
        calculating, for the first agent and the first clinical outcome, a first set of risk scores, wherein each risk score in the first set of risk scores corresponds to a risk score for a particular stratification category included in the plurality of stratification categories, and wherein calculating the risk score for a given stratification category includes measuring a statistical significance of a relationship between the first agent and the first clinical outcome for the patients included in the given stratification category;
        displaying, in response to the selection and on the display device in a second graphical user interface, a two-dimensional grid in which the first clinical outcome is displayed in a first axis and the plurality of stratification categories are displayed in a second axis; and
        displaying, in response to the selection and on the display device in the second graphical user interface, for each stratification category in which the first clinical outcome is observed, a graphical element in the two-dimensional grid for a corresponding risk score in the first set of risk scores for the combination of first agent and the first clinical outcome for the stratification category.

* * * * *